US008815939B2

(12) United States Patent
McComsey et al.

(10) Patent No.: US 8,815,939 B2
(45) Date of Patent: Aug. 26, 2014

(54) SUBSTITUTED SULFAMIDE DERIVATIVES

(75) Inventors: David F. McComsey, Warminster, PA (US); Michael H. Parker, Chalfont, PA (US)

(73) Assignee: Janssen Pharmaceutica NV, Beerse (BE)

( * ) Notice: Subject to any disclaimer, the term of this patent is extended or adjusted under 35 U.S.C. 154(b) by 397 days.

(21) Appl. No.: 12/502,472

(22) Filed: Jul. 14, 2009

(65) Prior Publication Data
US 2010/0063138 A1 Mar. 11, 2010

Related U.S. Application Data

(60) Provisional application No. 61/082,654, filed on Jul. 22, 2008.

(51) Int. Cl.
  A61K 31/357 (2006.01)
  C07D 319/16 (2006.01)
  A61P 25/22 (2006.01)

(52) U.S. Cl.
  USPC .......................................... 514/452; 549/366

(58) Field of Classification Search
  USPC .......................................... 514/452; 549/366
  See application file for complete search history.

(56) References Cited

U.S. PATENT DOCUMENTS

| | | |
|---|---|---|
| 2,527,861 A | 10/1950 | Walter |
| 3,143,549 A | 8/1964 | Lafferty et al. |
| 3,318,952 A | 5/1967 | Houlihan |
| 3,383,414 A | 5/1968 | Houlihan |
| 3,539,573 A | 11/1970 | Schmutz |
| 3,621,096 A | 11/1971 | Prange et al. |
| 4,513,006 A | 4/1985 | Maryanoff et al. |
| 4,539,413 A | 9/1985 | Mouzin et al. |
| 4,710,500 A | 12/1987 | Perregaard |
| 4,804,663 A | 2/1989 | Kennis et al. |
| 4,831,031 A | 5/1989 | Lowe, III et al. |
| 4,879,288 A | 11/1989 | Warawa et al. |
| 5,112,838 A | 5/1992 | Perregaard et al. |
| 5,158,952 A | 10/1992 | Janssen et al. |
| 5,192,785 A | 3/1993 | Lo et al. |
| 5,194,446 A | 3/1993 | Lo et al. |
| 5,212,326 A | 5/1993 | Meade |
| 5,229,382 A | 7/1993 | Chakrabarti et al. |
| 5,238,945 A | 8/1993 | Perregaard et al. |
| 5,242,942 A | 9/1993 | Costanzo et al. |
| 5,258,402 A | 11/1993 | Maryanoff |
| 5,273,993 A | 12/1993 | Lo et al. |
| 5,312,925 A | 5/1994 | Allen et al. |
| 5,384,327 A | 1/1995 | Costanzo et al. |
| 5,387,700 A | 2/1995 | Maryanoff et al. |
| 5,731,348 A | 3/1998 | Gu et al. |
| 5,753,693 A | 5/1998 | Shank |
| 5,753,694 A | 5/1998 | Shank |
| 5,760,007 A | 6/1998 | Shank et al. |
| 5,780,650 A | 7/1998 | Furukawa et al. |
| 5,935,933 A | 8/1999 | Shank et al. |
| 5,998,380 A | 12/1999 | Ehrenberg et al. |
| 6,071,537 A | 6/2000 | Shank |
| 6,150,419 A | 11/2000 | Fairbanks et al. |
| 6,187,338 B1 | 2/2001 | Caruso et al. |
| 6,191,163 B1 | 2/2001 | Cottrell |
| 6,211,241 B1 | 4/2001 | Islam et al. |
| 6,319,903 B1 | 11/2001 | Carrazana et al. |
| 6,322,503 B1 | 11/2001 | Sparhawk, Jr. |
| 6,323,236 B2 | 11/2001 | McElroy |
| 6,391,877 B1 | 5/2002 | Islam et al. |
| 6,503,884 B1 | 1/2003 | Ehrenberg et al. |
| 6,559,293 B1 | 5/2003 | Almarsson et al. |
| 6,562,865 B1 | 5/2003 | Codd et al. |
| 6,583,172 B1 | 6/2003 | Shank |
| 6,627,653 B2 | 9/2003 | Plata-Salaman et al. |
| 6,852,701 B2 | 2/2005 | Plata-Salaman et al. |
| 6,852,738 B2 | 2/2005 | Jones et al. |
| 6,949,518 B1 | 9/2005 | Chu |
| 8,084,490 B2 | 12/2011 | McComsey et al. |
| 2001/0008889 A1 | 7/2001 | Caruso et al. |
| 2002/0015713 A1 | 2/2002 | Murdock et al. |
| 2004/0073037 A1 | 4/2004 | Jones |
| 2004/0192690 A1 | 9/2004 | Buxton et al. |
| 2004/0253223 A1 | 12/2004 | Rodriguez |
| 2005/0148603 A1 | 7/2005 | Jimenez et al. |

(Continued)

FOREIGN PATENT DOCUMENTS

| | | |
|---|---|---|
| CA | 2416647 A | 1/2003 |
| DE | 1211166 | 2/1966 |

(Continued)

OTHER PUBLICATIONS

Aeberli, P. et al. "Neuropharmacological Investigation of N-Benzylsulfamides", Journal of Medicinal Chemistry, Jul. 1967, vol. 10, No. 4, pp. 636-642.
Ambrosini, P.J., Psychiatr. Serv. 2000, 51, 627-633.
American Diabetes Association, "Definition and Description of Diabetes Mellitus", Diabetes Care, Jan. 2006; p. S43-S48, vol. 29 Supplement 1.
Ananth, J., Psychother. Psychosom. 1998, 67, 61-70.
Angehagen, Mikael et al., "Does topiramate (TPM) have protective effects on astroglia cells and neurons in primary cortical cultures", Epilepsia, (1998) vol. 39, No. Suppl 6, pp. 44, XP000923162 abstract 2.050.
Ayata et al., "Suppression of cortical Spreading Depression in Migraine Prophylaxis", Ann Neurol 2006; 59:652-661.

(Continued)

Primary Examiner — Sreeni Padmanabhan
Assistant Examiner — Sahar Javanmard
(74) Attorney, Agent, or Firm — Hal B. Woodrow

(57) ABSTRACT

The present invention is directed to novel substituted sulfamide derivatives, pharmaceutical compositions containing said derivatives and the use of said derivatives form in the treatment of anxiety and related disorders; bipolar depression and mania; depression; epilepsy and related disorders; epileptogenesis; glucose related disorders; lipid related disorders; migraine; obesity; pain; substance abuse and as neuroprotective agents. The present invention is further directed to a process for the preparation of the novel substituted sulfamide derivatives.

14 Claims, No Drawings

(56) References Cited

U.S. PATENT DOCUMENTS

| | | |
|---|---|---|
| 2005/0282887 A1 | 12/2005 | McComsey et al. |
| 2006/0047001 A1 | 3/2006 | Parker et al. |
| 2006/0241172 A1 | 10/2006 | Zhou et al. |
| 2006/0270856 A1 | 11/2006 | Abdel-Magid et al. |
| 2006/0276528 A1 | 12/2006 | Parker et al. |
| 2007/0155821 A1 | 7/2007 | Smith-Swintosky et al. |
| 2007/0155822 A1 | 7/2007 | Smith-Swintosky et al. |
| 2007/0155823 A1 | 7/2007 | Smith-Swintosky et al. |
| 2007/0155824 A1 | 7/2007 | Smith-Swintosky |
| 2007/0155825 A1 | 7/2007 | Smith-Swintosky et al. |
| 2007/0155826 A1 | 7/2007 | Smith-Swintosky et al. |
| 2007/0155827 A1 | 7/2007 | Smith-Swintosky et al. |
| 2007/0191449 A1 | 8/2007 | Smith-Swintosky |
| 2007/0191450 A1 | 8/2007 | Smith-Swintosky |
| 2007/0191451 A1 | 8/2007 | Smith-Swintosky |
| 2007/0191452 A1 | 8/2007 | Smith-Swintosky |
| 2007/0191453 A1 | 8/2007 | Smith-Swintosky |
| 2007/0191459 A1 | 8/2007 | Smith-Swintosky |
| 2007/0191460 A1 | 8/2007 | Smith-Swintosky |
| 2007/0191461 A1 | 8/2007 | Smith-Swintosky |
| 2007/0191474 A1 | 8/2007 | Smith-Swintosky |
| 2007/0232685 A1 | 10/2007 | Fawzy et al. |
| 2007/0293440 A1 | 12/2007 | Smith Swintosky et al. |
| 2007/0293476 A1 | 12/2007 | Smith Swintosky et al. |
| 2008/0027131 A1 | 1/2008 | Smith-Swintosky et al. |
| 2009/0182141 A1 | 7/2009 | Abdel-Magid et al. |
| 2009/0209634 A1 | 8/2009 | Smith-Swintosky |
| 2009/0247616 A1 | 10/2009 | Smith-Swintosky et al. |
| 2009/0247617 A1* | 10/2009 | Abdel-Magid et al. ........ 514/452 |
| 2009/0247618 A1 | 10/2009 | Ballentine et al. |
| 2009/0318544 A1 | 12/2009 | Mehrman et al. |

FOREIGN PATENT DOCUMENTS

| | | |
|---|---|---|
| DE | 2022370 | 12/1971 |
| DK | 9800727 A | 5/1998 |
| EP | 138441 | 4/1985 |
| EP | 483881 B1 | 5/1992 |
| EP | 490689 | 6/1992 |
| EP | 498770 | 8/1992 |
| EP | 503440 A1 | 9/1992 |
| EP | 478954 | 10/2000 |
| EP | 1056733 | 12/2000 |
| EP | 1118610 | 7/2001 |
| GB | 1087602 | 10/1967 |
| GB | 1111706 | 5/1968 |
| RU | 2246727 | 4/2004 |
| RU | 2226357 | 8/2004 |
| WO | 94/14827 A1 | 7/1994 |
| WO | 95/17406 A1 | 6/1995 |
| WO | 96/06822 A1 | 3/1996 |
| WO | 97/13510 A1 | 4/1997 |
| WO | 97/19682 A1 | 6/1997 |
| WO | 97/19919 | 6/1997 |
| WO | 97/35584 A1 | 10/1997 |
| WO | 98/00123 | 1/1998 |
| WO | 98/00124 A1 | 1/1998 |
| WO | 98/00130 A2 | 1/1998 |
| WO | 98/00131 A1 | 1/1998 |
| WO | 98/06708 A1 | 2/1998 |
| WO | 98/07447 A1 | 2/1998 |
| WO | 98/15270 | 4/1998 |
| WO | 99/44581 A2 | 9/1999 |
| WO | 99/62522 | 12/1999 |
| WO | 00/01376 A2 | 1/2000 |
| WO | 00/07583 A2 | 2/2000 |
| WO | 00/42995 A2 | 7/2000 |
| WO | 00/42996 A2 | 7/2000 |
| WO | 00/49017 | 8/2000 |
| WO | 00/50020 A2 | 8/2000 |
| WO | 00/54588 A1 | 9/2000 |
| WO | 00/61137 | 10/2000 |
| WO | 00/61139 A1 | 10/2000 |
| WO | 00/61140 A1 | 10/2000 |
| WO | 00/66109 A2 | 11/2000 |
| WO | 00/76493 A1 | 12/2000 |
| WO | 01/13904 A2 | 3/2001 |
| WO | 01/76576 A2 | 10/2001 |
| WO | 02/03984 | 1/2002 |
| WO | 02/07821 | 1/2002 |
| WO | 02/09694 | 2/2002 |
| WO | 02/30881 | 4/2002 |
| WO | 02/089785 | 11/2002 |
| WO | 02/096424 A1 | 12/2002 |
| WO | 2004/014352 | 2/2004 |
| WO | 2004/093912 A1 | 4/2004 |
| WO | 2004/092116 A1 | 10/2004 |
| WO | 2004/096771 A1 | 11/2004 |
| WO | 2004/098584 A1 | 11/2004 |
| WO | 2005/020917 A2 | 3/2005 |
| WO | 2006/007435 | 1/2006 |
| WO | 2006/007436 | 1/2006 |
| WO | 2006/010008 A1 | 1/2006 |
| WO | 2006/010750 A1 | 2/2006 |
| WO | 2006/023861 A1 | 3/2006 |
| WO | 2006/127184 | 11/2006 |
| WO | 2007/075695 | 7/2007 |
| WO | 2007/075698 | 7/2007 |
| WO | 2007/075717 | 7/2007 |
| WO | 2007/075751 | 7/2007 |
| WO | 2007/075752 | 7/2007 |
| WO | 2007/075833 | 7/2007 |
| WO | 2007/075834 | 7/2007 |
| WO | 2007/092086 | 8/2007 |
| WO | 2007/095615 | 8/2007 |
| WO | 2007/095618 | 8/2007 |
| WO | 2007/098486 | 8/2007 |
| WO | 2007/137167 | 11/2007 |
| WO | 2009/089210 | 7/2009 |
| WO | 2009/120191 | 10/2009 |
| WO | 2009/120192 | 10/2009 |

OTHER PUBLICATIONS

Barry et al. Current status of the utilization of antiepileptic treatments in mood, anxiety and aggression: drugs and devices, Jan. 2004, 35, 1.

Beck-Nielsen H., "In Vivo Glucose Metabolism, Insulin Secretion and, Insulin Action in Europids with Non-insulin-dependent Diabetes Mellitus (NIDDM) and Their First-degree Relatives", Diabet Med Sep. 1996; 13(9 Suppl 6):S78-84.

Berman, R.M. et al., Depress. Anxiety 1997, 5, 154-164.

Besag et al. "Behavioural Effects of the New Anticonvulsants" Drug Safety, ADIS Press, Auckland, NZ, vol. 24, No. 7, 2001, pp. 513-536.

Breslau et al., "The impact of migraine. Epidemiology, risk factors, and comorbidities" Neurology, 2001; 56:S4-S12 (Abstract only).

Burton et al. Anti-epileptic drugs for pain management. Pain, Symptom, Control and Palliative Care, 2001, vol. 1, No. 2.

Ca 835894-69-4 Sulfamide (1,3-benzodioxol-2-ylmethyl) (2005).

CA PLUS 835894-63-8 Sulfamic acid (3,4-dihydro-2H-1-benzopyran-2-yl)methyl ester (2005).

CA PLUS 835894-65-0 Sulfamide [(3, 4-dihydro-2H-1-benzopyran-2-yl) methyl] (2005).

CA PLUS 835894-67-2 Sulfamic acid (1,3-benzodioxol-2-ylmethyl ester) (2005).

Cadieux, R.J., Am. Fam. Physician 1998, 58, 2059-2062.

Calabrese, J.R. et al., Eur. Neuropsychopharmacol. 1999, 9, S109-S112.

Calabresi et al., "Antiepileptic drugs in migraine: from clinical aspects to cellular mechanisms", TRENDS in Pharmacological Sciences, vol. 28, No. 4, 188-195 (2007).

Caumo A., "Insulin Sensitivity from Meal Tolerance Tests in Normal Subjects: A Minimal Model Index", J Clin Endocrinol Metab, 85(11):4396-402 2000.

Cavaletti G et al: "Experimental peripheral neuropathy induced in adult rats by repeated intraperitoneal administration of Taxal", Exper Neurol 133:64-72, 1995.

Chaplan Sr et al: "Quantitative assessment of tactile allodynia in the rat paw". J Neurosci Meth, 53:55-63, 1994.

Crooke et al, Abstract, Topiramate Improves Glycemic Control Independent of Weight Loss in ob/ob Mice.diabetes. A Journal of the

(56) References Cited

OTHER PUBLICATIONS

American Diabetes Association, Abstract Book 61$^{st}$ Scientific Sessions Friday, Jun. 22-Tuesday Jun. 26, 2001, 2158-PO, A513.
Demarest et al, Abstract, Topiramate Improves Glucose Tolerance and May Improve Insulin Sensitivity in Animal Models of Type 2 Diabetes Mellitus, diabetes, A Journal of the American Diabetes Association, Abstract Book 61st Scientific Sessions Friday, Jun. 22-Tuesday Jun. 26, 2001, 1254-P, A302.
Diamond et al, "Practical Approaches to Migraine Management", 2002, CNS Drugs, 16(6), pp. 385-403.
Dickenson et al. Neurobiology of neuropathic pain: mode of action of anticonvulsants. European Journal of Pain, 2002, 6 (Suppl. A): 51-60, 2002.
Dinneen S.F., "The Postprandial State: Mechanism of Glucose Intolerance", Diabet Med Aug. 1997; 14 Suppl 3:S19-24.
Drach, B.S. et al.: "N-1,2,2,2,-tetra-chloroethyl-N',N'-dimethylsulphamide" . Journal of Organic Chemistry of the USSR., vol. 13, No. 7, Jul. 1977, pp. 1289-1294, XP008067470.
Dressler et al., Benzodiazepine in geriatric patients . . . , Abstract, Anaesthesiologie and reanimation, 1996, vol. 21/5, pp. 136-138.
Drug Facts and Comparison (1995 Edition, pp. 1607).
Dursun, S.M. et al., "Accelerated weight loss after treating refractory depression with fluoxetine plus topiramate: possible mechanisms of action?", The Canadian Journal of Psychiatry, vol. 46, No. 3, pp. 287-288, 2001.
Edwards, K.R. et al, Efficacy and safety of topiramate in the treatment of painful diabetic neuropathy: a double-blind placebo-controlled study ADIS Title: Topiramate: therapeutic use: Neurogenic pain; In patients with diabetic neuropathy: Neurology 54 (Suppl. 3): 81 Apr. 11, 2000.
Edwards, et al., Evaluation of Topiramate in the Management of Painful Diabetic Neuropathy. Presented at: 18$^{th}$ Annual Meeting of the American Pain Society; 1998, Fort Lauderdale, FL.
Emancipator K., "Laboratory Diagnosis and Monitoring of Diabetes Mellitus", Am J Clin Pathol, 112(5):665-74 1999.
Erfurth, Andreas et al., "Bupropion as add-on strategy in difficult-to-treat bipolar depressive patients", Neuropsychobiology, vol. 45, No. Sup 1, pp. 33-36, 2002.
Fakhoury et al., Epilepsy Behav. Aug. 2007, abstract.
Flatters, SJL et al: "Acetyl-L-carnitine prevents and reduces paclitaxel-induced painful peripheralneuropathy", Neurosci Lett 397:219-223, 2006.
Gareri, P. et al, Progress in Neurobiology 61, 2000, 353-396.
Garonna, F. et al., "Topiramate in the treatment of overweight/obese binge eaters ADIS Title: Topiramate: therapeutic use; Obesity; In patient with binge eating disorders" International Journal of Neuropsychopharmacology 3(Suppl 1): 299: Jul. 2000 XP001030426 Bassano dG Vicenza Italy, whole document.
Ghaemi et al., Soc. of Bio. Psychiatry, (1999) vol. 45, 137-144.
Goldberg R.G., "Prevention of Type 2 Diabetes", Med Clin North Am, Jul. 1998; 82(4):805-21.
Gorelick D A, "Pharmacological treatment" Recent Developments in Alcoholism, vol. 11, 1993, p. 413-427, XP00913482 p. 417.
Gorelick et al., Drugs 2004: 64(14), pp. 1547-1573.
Grond et al., "Weak Opioids—an educational substitute for morphine?", Current Opinion in Anaesthesiology, vol. 11, No. 5, 1998, pp. 559-565 XP00982759.
Groop L., "Characterization of the Prediabetic State", Am J Hypertension; Sep. 1997; 10(9 Pt 2):172S-180S.
Guillaume et al., "Glial contribution to seizure: Carbonic anhydrase activity in epileptic mammalian brain" Epilepsia, 1991, vol. 32, No. 1, 1991, pp. 10-15.
Haffner S.M., "Impaired Glucose Tolerance, Insulin Resistance and Cardiovascular Disease", Diabetic Medicine, Aug. 1977; 14 Suppl 3:S12-8.
Haffner S.M., "The Prediabetic Problem: Development of Non-Insulin-Dependent Diabetes Mellitus and Related Abnormalities", J Diabetes Complications, Mar.-Apr. 1997; 11(2):69-76.
Harrison's Principles of Internal Medicine, Isselbacher et al. eds. McGraw-Hill, Inc., New York, 1994, p. 69.

Harrison'S Principles of Internal Medicine, vol. 2, 23d ed., Ed by Isselbacher, Braunwald, Wilson, Martin, Fauci and Kasper, McGraw-Hill Inc New York City, 1994, p. 2275.
Hatzinger, M. et al., Wien. Med. Wochenschr. 1999, 149, 511-514.
Hauner H, "Managing type 2 diabetes mellitus in patients with obesity," Treatments in Endocrinology, 2004, 3(4), 223-232 (only abstract provided).
Headache Classification Committee of the International Headache Society. Cephalalgia 1988; 8 Suppl 7:1-96.
Hering et al., "Sodium valproate in the treatment of cluster headache", Cephalalgia (Sep. 1989) 9(3) pp. 195-198.
Huisman, M. et al.: "Synthesis of N-(diemthylsulphamoyl)aldimines, a new type of aldimine derivative". Synthetic Communications, vol. 27, No. 6, 1997, pp. 945-952.
Jay et al., "Epilepsy, Migraine and EEG Abnormalities in Children: a Review & Hypothesis," Journal of Head and Face Pain, abstract, vol. 22, Issue 3, pp. 110-114, 1982.
Joffe, R.T. et al., Arch. Gen. Psychiatry 1993, 50, 397-393.
Johns Hopkins Clinical Trial of Topiramate for Cocaine Addiction (ClinicalTrials.gov), 2009.
Johnson, B A: "Progress in the development of topiramate for treating alcohol dependence: From a hypothesis to a proof-of-concept study" Alcoholism: Clinical and Experimental Research 2004 United States, vol. 28, No. 8, 2004, pp. 1137-1144.
Johnson, SA CNS Drugs, 2005. vol. 19, No. 1 0, pp. 873-896.
Kawasaki, "Structural and functional analysis of pancreatic islets preserved by pioglitazone in db/db mice", Am J Physiol Endocrinol Metab; 2004, p. E510-E518, doi 10.1152/ajpendo.00128.2004.
Keck, P et al, "Valproate and carbamazepine in the treatment of panic and post traumatic stress disorders, withdrawals states . . . " J Clin Psychopharm, vol. 12, No. 1, p. 36S-41S, 1992.
Kent, J.M., Lancet 2000, 355, 911-918.
Ketter, T.A. et al., J. Clin. Psychiatry 1995, 56, 471-475.
Keung W.M. et al, "Daidzin and daidzein suppress free-choice ethanol intake by Syrian golden hamsters" Proc Natl Acad Sci, vol. 90, p. 1008-10012, Nov. 1993.
Klinger et al., "Inhibition of carbonic anhydrase-II by sulfamate and sulfamide groups: An investigation involving direct thermodynamic binding measurements" Journal of Medicinal Chemistry, vol. 49, No. 12, 15 Jun. 2006, pp. 3496-3500.
Kohno, H. et al.: "A Novel Synthesis of Isoquinolines Containing an Electron Withdrawing Substitute". Heterocycles, vol. 51, No. 1, 1999, pp. 103-117, XP008052600.
Kralinsky E.A. Tramal in the treatment of pain in children with malignancies, Klinicka Onkologie, vol. 7, No. 6, 1994, pp. 182-185 (See English Abstract provided).
Kunkler et al., "Hippocampal Spreading Depression Bilaterally Activates the Caudal Trigeminal Nucleus in Roadent", Hippocampus 13:835-844 (2003).
Kuzniecky et al., "Topiramate increases cerebral GABA in healthy humans", Neurology (Aug. 1998) 51(2) pp. 627-629.
Kyowa Hakko, "Topiramate" Drugs of the Future, ES, Barcelona, vol. 21, No. 4, Jan. 1, 1996; p. 463-465.
Langtry H.D. et al, "Topiramate, A review of its pharmacodynamic and pharmacokinetic properties and clinical efficacy in the management of epilepsy" Drugs, (1997) 54/5 pp. 752-773, XP002179441.
Lydiard, R.B. et al., J. Clin. Psychiatry 1998, 59, Suppl. 18, 10-17.
Malatynska et al., "Dominant-submissive behavior as models of mania and depression", Neuroscience and Biobehavioral Review, 29 (2005) 715-737.
Malatynska et al., "Submissive behavior in mice as a test for antidepressant drug activity", Neuroscience and Biobehavioral Review, 82 (2005) 306-313.
Maryanoff et al., J. Med. Chem., vol. 48, No. 6, pp. 1941-1947 (2005).
Maryanoff et al.: Anticonvulsant O-Alkyl Sulfamates 2,3:4,5-Bis-O-(1-methylethylidene)-betas-D-fructopyranose Sulfamate and Related Compounds, J.Med. Chem., vol. 30, No. 5, 1987, pp. 880-887.
Maryanoff, B.E.et al.: "Structure-Activity Studies on Anticonvulsant Sugar Sulphmates Related to Topiramate. Enhanced Potency with Cyclic Sulphate Derivatives". Journal of Medicinal Chemistry, vol. 41, No. 8, 1998, pp. 1315-1343.

(56) References Cited

OTHER PUBLICATIONS

Mathew, Ninan T., Md, et al, "Prophylaxis of Migraine, Transformed Migraine, and Cluster Headache with Topiramate" Headache (2002), (42)796-803.
Mathew, N. T. "Antiepileptic Drugs in Migraine Prevention", 2001, Headache, Nov./Dec. Suppl 2001, pp. S18-S24.
Mazzotta et al., J Headache Pain, 2004 5:S67-S70.
McElroy, S.L. et al., "A pilot trial of adjunctive topiramate in the treatment of bipolar disorder ADIS Title: Topiramate: therapeutic use; Bipolar disorder: A pilot trial of adjunctive treatment" retrieved from STN Database Accession No. 1998:39968 XP00217779443 Abstract & XXIST CINP Congress (Jul. 12, 1998) pp. 281 (Poster) University of Cincinnati College of Medicine, Cincinnati, OH.
Meldrum B. et al., "Excitatory amino acid neurotoxicity and neurodegenerative disease" TIPS, vol. 11, 1990, pp. 379-387, XP000915223.
Migraine: Treatments and drugs, by Mayo Clinic Staff, http://www.mayoclinic.com/health/migraineheadache/DS00120/Dsection=treatment-and-drugs, 2009.
Moller, H.J. et al., Eur. Arch. Psychiatry Clin. Neurosci. 2000, 250, 57-68.
Moskowitz, M.A., "The Neurobiology of Vascular Head Pain", Annals of Neurology, vol. 16, Issue 2, pp. 157-168, 1984.
Mueller T I, "A double-blind, placebo-controlled pilot study of carbamazepine for the treatment of alcohol dependence", Alcoholism Clin Exp Res, vol. 21, No. 1, 1997, p. 86-92.
Mula et al., "The role of anticonvulsant drugs in anxiety disorders: a critical review of the evidence" Journal of Clinical Psychopharmacology, Williams and Wilkins, vol. 1.27, No. 3, 2007, pp. 263-272.
Myers, R.D., "New Drugs for the Treatment of Experimental Alcoholism", Alcohol, vol. 11, No. 6, 1994, p. 439-451.
Nemeroff, C.B., Depress. Anxiety 1996-1997, 4, 169-181.
Nickel et al., Journal of Affective Disorders, vol. 87(2-3), 2005, pp. 243-252.
Nies et al., Goodman & Gilman's The Pharmacological Basis of Therapeutics, 9th Edition, pp. 43-62, 1996.
Olesen et al., "Spreading Cerebral Oligemia in Classical- and Normal Cerebral Blood Flow in Common Migraine", Department of Neuromedicine, Rigshospitalet 2100 Copenhagen, Denmark, Jan. 28, 1982 (Headache 22:242-248, 1982).
Olson et al [Editors]. Remington's Pharmaceutical Sciences, pp. 420-425, 1980.
Osborne et al, Abstract, Topiramate Improves Glycemic Control and Triglycerides in Animal Models 1 p. The Posters were presented at the American Diabetes Association Conference held Jun. 22-26 in Philadelphia, diabetes, A Journal of the American Diabetes Association, Abstract Book 61st Scientific Sessions Friday, Jun. 22-Tuesday Jun. 26, 2001, 1255-P, A302.
Ottman et al., "Comorbidity of migraine and epilepsy", Neurology, 1994;44: 2105 (Abstract only).
Pansare, S.V. et al.: "Intramolecular Imine Cross-Coupling in Dibenzylidine Sulphamides; synthesis of unsymmetrical 1,2-diaryl ethanediamines". Tetrahedron Letters, vol. 37, No. 16, Apr. 15, 1996, pp. 2859-2862 (2005).
Pascual D et al: "A cannabinoid agonist, WIN55,212-2, reduces neuropathic nocicipetion induced by paclitaxel in rats" Pain 118:23-34, 2005.
Penovich et al., "Weight Loss in Patients Receiving Topiramate for Intractable Epilepsy", 1994, Neurology 44 (Suppl. 2) Abstract 309P, 46th Annual Meeting of the American Academy of Neurology, Washington, D.C.
Perry et al. "Sumatriptan: An Updated Review of its Use in Migraine", 1998, Drugs, vol. 55, No. 6, pp. 889-922.
Pini et al., "Anti-Epileptic Drugs in the Preventive Treatment of Migraine Headache: a Brief Review", (J. Headache Pain, 2001, 2:13-19.
Polomano et al: "A painful peripheral neuropathy in the rat produced by the chemotherapeutic drug, paclitaxel", Pain, 94:293-304, 2001.

Prado Lima, P.A.S. et al., "Topiramate in treatment-refractory depression" retrieved from STN Database accession No. 1999:61852 XP002179442 Abstract & 11th World Congress of Psychiatry (Aug. 6, 1999), vol. 2,00.126.
Raguraman, et al., "Effects of topiramate in alcohol dependence [2]" Australian and New Zealand Journal of Psychiatry, 2005 Australia, vol. 39, No. 8, 2005, pp. 736-737.
Ramlo-Halsted BA, "The Natural History of Type 2 Diabetes", Primary Care Dec. 1999; 26(4):771-89.
Reis et al. Craving decrease with topiramate in outpatient treatment for cocaine dependence: an open label trial, Rev Bras Psiquiatr 2008;30(2):132-5.
Rogaswki et al., Nature Medicine, vol. 10, No. 7, Jul. 2004, pp. 685-692.
Rogawski et al., Nature Reviews Neuroscience, vol. 5 (1), 2004, pp. 553-564.
Rost et al., The effect of tramadol and other analgesics on the pain . . . , Abstract, Arzneim-Forsch. 1978, vol. 28 (1a0 pp. 181-183).
Rouillon, F., Eur. Neuropsychopharmacol 1999, 9 Suppl. 3, S87-S92.
Rygula et al., "Anhedonia and motivational deficits in rats: Impact of chronic social stress", Behavioral Brain Research, 162 (2005) 127-134.
Sanacora, G. et al., "Impairment of GAB Aergic transmission in depression: New Insights from neuroimaging studies", Critical Reviews in Neurobiology, (2000) 14/1 pp. 23-45, XP001029967, whole document.
Scozzafava a et al, "Modulaton of Carbonic Anhydrase Activity and Its Applications in Therapy", Expert Opinion on Therapeutic Patents 2003 United Kingdom, vol. 14, No. 5 (2004) pp. 667-702, XP002331413, ISSN:1354-3776.
Shank et al., "Examination of two independent kinetic assays for determining the inhibition of carbonic anhydrases I and II: Structure-activity comparison of sulfamates and sulfamides" Chemical Biology and Drug Design, vol. 68, No. 2, 2006, pp. 113-119.
Sharma K, McCue P, Dunn Sr. Am J Physiol Renal Physiol. Jun. 2003; 284(6):F1138-44.
Silberstein et al., "Migraine & Epilepsy", www.myepilepsy.com, 2002.
Sofuoglu et al., CNS Drugs 2005: 19(1), pp. 13-25.
Soledade et al.:"Toward the control of Leptosphaeria Maculans" Design, Synthesis, biological activity, and metabolism of potential detoxification inhibitors of the crucifer phytoalexin brassinin. Bioorganic & Medicinal Chemistry, vol. 14, No. 14, Apr. 17, 2006, pp. 4958-4979, XP005458688.
Stephen, Linda J. et al., "Lamotrigine and topiramate may be a useful combination", The Lancet, vol. 351, No. 9107, pp. 958-959, 1998.
Stephen, Linda J. et al., "Topiramate in Refractory Epilepsy: A Prospective Observational Study", Epilepsia, vol. 41, No. 8, pp. 977-980, 2000.
Stoll et al., Harvard Rev. Psychiatry, Jul./Aug. 1996, vol. 4, No. 2, 77-89.
Storey et al, "Topiramate in Migraine Prevention: A Double Blind, Placebo-Controlled Study", 2001, Headache, 41, pp. 968-975.
Swinyard et al., Antiepileptic Drugs, Third Edition, pp. 85-102, 1989.
Ten Have, R. et al.:"Novel Synthesis of 4(5)-monosubstituted imidazoles via cycloaddition of tosylmethyl isocyanide to aldimines". Tetrahedron, vol. 53, No. 33, Aug. 18, 1997, pp. 11355-11368, XP004106007.
Tenovuo, O. "Central Acetylcholinesterase Inhibitors in the Treatment of Chronic Traumatic Brain Injury-Clinical Experience in 111 Patients". Progress in Neuro-Psychopharmacology and Biological Psychiatry 2005 US, vol. 29, No. 1, Jan. 2005, pp. 61067. XP002431412.
The Merck Manual (1987), Merck Sharp & Dohme Research Laboratories, Rahway, NJ XP002144176, pp. 1351-1356.
The Merck Manual, 1999, Merck Research, Whitehouse Station, NJ XP002224345, Diabetes Mellitus, pp. 165-177.
Topiramate retrieved from STN Database Accession No. 1998:2562 XP002179444 Abstract & R&D Focus Drug News, Jul. 27, 1998.
Traube, W. et al.: "Zur Kenntnis des Sulfamids". Berichte der Deutschen Chemischen Gesellschaft, vol. 56, 1923, pp. 1656-1663, XP002393747.
Uhart et al., Addiction Biology, 14, pp. 43-64, 2008.

(56) References Cited

OTHER PUBLICATIONS

Uys et al., CNS Neurol Disord Drug Targets, 7(5), 2008, pp. 482-91.
Van Amerigen et al. Antiepileptic drugs in the treatment of anxiety disorders: Role in Therapy, Drugs, 2004, 64(19), 2199-2220.
Vandi, A., et al.: "Synthesis and Properties of Some N-Substituted Sulphamides", Journal of Organic Chemistry, vol. 26, No. 4, Apr. 1961, pp. 1136-1138, XP002394144.
Seggern, Randal L., et al, "Efficacy of Topiramate in Migraine Prophylaxis: A Retrospective Chart Analysis" Headache (2002), (42)804-809.
Waugh et al., "Topiramate: As Monotherapy in Newly Diagnosed Epilepsy" CNS Drugs, vol. 17, No. 13, 2003, pp. 985-992.
Wauquier a et al, "Topiramate: A potent anticonvulsant I the Amygdala-Kindled Rat" Epilepsy Research, NJ, Elsevier Science Publishers, Amsterdam, vol. 24, No. 2, Jun. 1, 1996, p. 73-77, XP002042953.
WebMD Medical News Epilepsy Drugs Fights Migraine, 2002, www.webmd.com/migraine-headaches/news/20020923/epilepsydrug-fights-migraine.
Weib, G. et al.: "Herstellung und Reaktionen von N-Monoalkylamidosulfonylchloriden" Liebigs Annalen Der Chemie, vol. 729, Dec. 1969, pp. 40-51, XP002187581 (see English Abstract provided).
Wheeler et al., "Topiramate-treated cluster headache", Neurology (Jul. 1999) vol. 53, No. 1 pp. 234-236.
Wheeler S.D., "Antiepileptic Drug therapy in Migraine Headache", Current Treatment Options Neurology, Sep. 2002; 4(5):383-394.
Wheeler, "Significance of migrainous features in cluster headache", Headache (1998) 38/7 pp. 547-551.
Whitehead, C.W. et al.: "Diuretics. II. Alkoxymercuration oby mixed anion sales of mercury". Journal of the American Chemical Society, vol. 80, No. 9, May 5, 1958, pp. 2182-2185, XP002393746.
Williams, Jr., J.W., et al., Ann. Intern. Med. 2000, 132, 743-756.
Winhusen et al. Drug and Alcohol Dependence 91 (207) 131-148, 2007.
Yang Y. et al., "Neuroprotection by delayed administration of topiratmate in rat model of middle cerebral artery embolization", Brain Research, vol. 804, No. 2, 1998, pp. 169-176, XP000921218.
York, Da et al, "Effects of Topirament on High Fat Diet-Induced Obesity", FASEB journal, Fed. Of America Soc. For Experimental Biology, Bethesda, MD, US., vol. 14, No. 4, Apr. 2000. p. A431, XP000915192.
Young, WB et al, "Topiramate: a case series study in migraine prophylaxis" Cephalalgia (2002), (22)659-663.
Ziegler. E., et al.:"Zur Reaktivitat von C=Ndoppelbindungssytemen, VI. Reaktionen mit Sulfonamiden und Sulfamiden". Zeitschrift Fur Naturforschung, vol. 30B, 1975, pp. 951-953, XP008067475.
Alcaraz et al., Org. Lett., 2004, 6(16), pp. 2705-2708.
Beaudoin et al., J. Org. Chem., 2003, 68, pp. 115-119.
Birch et al., J. Med. Chem., 1999, 42, pp. 3342-3355.
Delgado et al., Tet Lett, 1988, 29(3), pp. 3671-3676.
Estave et al., Tet Lett, 2002, 43, pp. 1019-1021.
Gavernet et al., Bioorg & Med Chem., 2007, 15, pp. 5604-4516.
Hedayatullah et al., Phosphorus and Sulfur, 1985, 25(1), pp. 33-38.
Hirayama et al., Bioorg & Med Chem., 2002, 10, pp. 1509-1523.
Kim et al., Tet Lett, 23(14), pp. 1505-1508, 1982.
Kubicki et al., J Mol Struct., 2001, 531(1-3), p. 65-70.
Lee et al., Org. Chem 1990 55(25) pp. 6098-6104.
Muniz et al., Synlett, 2005, 1, pp. 149-151.
Nelson et al., J. Med. Chem., 1977, 20(7), pp. 880-885.
Nelson et al., J. Med. Chem., 1979, 22(9), pp. 1125-1127.
Nicolaou et al., Chem. Eur. J., 2004, 10, pp. 5581-5606.
Okada et al., Tet Lett, 2000, 41, pp. 7047-7051.
Park et al., J. Med. Chem., 2002, 45, pp. 5295-5302.
Winum et al., Org. Lett., 2001, 3(14), pp. 2241-2243.
Xu et al., SYNLETT, 2004, 11, pp. 1901-1904.
Zhong et al., J. Comb. Chem., 2004, 6, pp. 556-563.
Chemische Berichte 1959 92 pp. 509-513 (See English translation provided).
Agrawal et al., Bioorganic and Medicinal Chemistry, 11(2003), pp. 5353-5362.
Casini et al., Bioorganic and Medicinal Chemistry Letters, 13(2003), pp. 841-845.
Pasorekova et al., Journal of Enzyme Inhibition and Medicinal Chemistry, Jun. 2004, vol. 19(3), pp. 199-229.
Supuran et al., Curr. Med. Chem.—Cardiovascular and Hematological Agents, 2004, 2, pp. 49-68.
Supuran et al., Curr. Med. Chem.—Imm., Endoc. & Metab Agents, 2001, 1, 61-97.
Supuran et al., Exp. Opin. Ther. Patents, (2000), 10(5), pp. 575-600.
Supuran et al., Exp. Opin. Ther. Patents, (2002), 12(2), pp. 217-242.
Supuran et al., Medicinal Research Reviews, vol. 23, No. 2, pgs. 146-189, 2003.
Thakur at al., Bioorganic and Medicinal Chemistry, 12(2004), pp. 789-793.
Behl et al., Endocrinology, vol. 138, No. 1, pp. 101-106, 1997.
Coyle et al., Science, vol. 262, Issue 5134, pp. 689-695, 1993.
Desagher et al., The Journal of Neuroscience, 1996, 16(8), pp. 2553-2562.
Tabner et al., The Journal of Biological Chemistry, vol. 280, No. 43, pp. 35789-35792, Oct. 28, 2005.
Taylor et al., Science, vol. 296, pp. 1991-1995 (2002).
New England Journal of Medicine, vol. 342:505-507, 2001.
Merck Manuals Online Medical Library, www.merck.com, 2007.
Cleeves et al., "Trazodone is ineffective in essential tremor", J. Neurol Nerusurg Psychiatry, 1990, 53:268-269.
Koller et al., "Essential Tremor Variants: Effect of Treatment", abstract, Clinical Pharmacology, 1987.
Robinson et al. "Pregablin not Effective for Essential Tremor", www.medpagetoday.com, 2009.
Handley and Mithani, Naunyn. Schmied. Arch. Pharmacol., 327, 1-5, 1984.
Aron et al., Neuropharmacology, 10, 459-469, 1971.
Meert et al., Pharmacol. Biochem. Behav.; 2005, 80(2), pp. 309-326.
MacDonald et al., CNS Drugs, 2002, 16(8): 549-562.
Walden et al., Neuropsychobiology, 1998,38: 181-84.
Byrn et al., Pharmaceutical Research, Kluwer Academic Publishers, New York, NY, US, vol. 12, No. 7, 1995, pp. 945-954.
Bernando, L., Prevention of epilepsy after head trauma: do we need drugs or a new approach?, 2003, Epilepsia, 44, (Suppl. 10), 27-33.
D'Ambrosio et al., Curr. Opin. Neurol. Dec. 2004; 17(6): 731-735.
Jones et al. "Screening for Major Depression in Epilepsy with Common Self-Report Depression Inventories", Epilepsia, May 2005; 46(5):731-735.
Kane et al., Psychopharmacological Bulletin, vol. 24, pp. 62-67 (1988).
Kaplan & Sadock's Comprehensive Textbook of Psychiatry, Seventh Edition, vol. II, Lippincott Williams & Wilkins: Philadelphia, pp. 2467-2468, 2000.
Kaplan & Sadock's Comprehensive Textbook of Psychiatry, Seventh Edition, vol. II, Lippincott Williams & Wilkins: Philadelphia, pp. 2470-2471, 2000.
Physician's Desk Reference; Kaplan & Sadock's Comprehensive Textbook of Psychiatry, Seventh Edition, vol. II, Lippincott Williams & Wilkins: Philadelphia, pp. 2466-2467, 2000 (olanzapine).
Physician's Desk Reference; Kaplan & Sadock's Comprehensive Textbook of Psychiatry, Seventh Edition, vol. II, Lippincott Williams & Wilkins: Philadelphia, pp. 2456-2463, 2000 (clozapine).
Physician's Desk Reference; Kaplan & Sadock's Comprehensive Textbook of Psychiatry, Seventh Edition, vol. II, Lippincott Williams & Wilkins: Philadelphia, pp. 2463-2466, 2000 (risperidone).
Physician's Desk Reference; Kaplan & Sadock's Comprehensive Textbook of Psychiatry, Seventh Edition, vol. II, Lippincott Williams & Wilkins: Philadelphia, pp. 2469-2470, 2000 (quetiapine).
Harwood, AJ, Molecular Psychiatry (2005) 10,117-126.
Goodman and Gilman's The Pharmacological Basis of Therapeutics, Eleventh Edition, McGraw Hill, Hypnotics and Sedatives, Chapter 16, pp. 401-427 (2006).
Goodman and Gilman's The Pharmacological Basis of Therapeutics, Eleventh Edition, McGraw Hill, Hypnotics and Sedatives, Chapter 17, pp. 429-459 (2006).

(56) References Cited

OTHER PUBLICATIONS

Goodman and Gilman's The Pharmacological Basis of Therapeutics, Eleventh Edition, McGraw Hill, Hypnotics and Sedatives, Chapter 19, pp. 429-459 (2006).
Sullivan, P., Epilepsy & Behavior 7 (2005) S12-S17.
Office Action mailed Mar. 26, 2008 in U.S. Appl. No. 11/154,443.
Notice of Allowance mailed Dec. 31, 2008 in U.S. Appl. No. 11/154,443.
Notice of Allowance mailed Jun. 8, 2009 in U.S. Appl. No. 11/154,443.
Notice of Allowance mailed Oct. 9, 2009 in U.S. Appl. No. 11/154,443.
Notice of Allowance dated Feb. 9, 2010 in U.S. Appl. No. 11/154,443.
Notice of Allowance dated May 25, 2010 in U.S. Appl. No. 11/154,443.
Notice of Allowance dated Sep. 20, 2010 in U.S. Appl. No. 11/154,443.
Notice of Allowance dated Jan. 25, 2011 in U.S. Appl. No. 11/154,443.
Notice of Allowance dated May 4, 2011 in U.S. Appl. No. 11/154,443.
Notice of Allowance dated Aug. 12, 2011 in U.S. Appl. No. 11/154,443.
Office Action mailed Oct. 3, 2007 in U.S. Appl. No. 11/154,386.
Office Action mailed Jul. 9, 2008 in U.S. Appl. No. 11/154,386.
Notice of Allowance mailed Mar. 6, 2009 in U.S. Appl. No. 11/154,386.
Notice of Allowance mailed Sep. 10, 2009 in U.S. Appl. No. 11/154,386.
Notice of Allowance dated Feb. 23, 2010 in U.S. Appl. No. 11/154,386.
Notice of Allowance dated Oct. 22, 2010 in U.S. Appl. No. 11/154,386.
Office Action mailed Apr. 14, 2008 in U.S. Appl. No. 11/209,122.
Notice of Allowance mailed Oct. 30, 2008 in U.S. Appl. No. 11/209,122.
Office Action mailed Mar. 20, 2009 in U.S. Appl. No. 11/209,122.
Notice of Allowance mailed Sep. 24, 2009 in U.S. Appl. No. 11/209,122.
Notice of Allowance mailed Jan. 13, 2010 in U.S. Appl. No. 11/209,122.
Notice of Allowance mailed Jan. 11, 2011 in U.S. Appl. No. 11/209,122.
Notice of Allowance mailed Jun. 1, 2011 in U.S. Appl. No. 11/209,122.
Notice of Allowance mailed Oct. 18, 2011 in U.S. Appl. No. 11/209,122.
Office Action mailed Sep. 10, 2008 in U.S. Appl. No. 11/406,794.
Notice of Allowance dated Mar. 13, 2009 in U.S. Appl. No. 11/406,794.
Notice of Allowance dated Jul. 17, 2009 in U.S. Appl. No. 11/406,794.
Office Action mailed Nov. 2, 2009 in U.S. Appl. No. 11/406,794.
Notice of Allowance dated Mar. 17, 2010 in U.S. Appl. No. 11/406,794.
Notice of Allowance dated Jul. 1, 2010 in U.S. Appl. No. 11/406,794.
Notice of Allowance dated Nov. 29, 2010 in U.S. Appl. No. 11/406,794.
Notice of Allowance dated Mar. 14, 2011 in U.S. Appl. No. 11/406,794.
Notice of Allowance dated Jun. 30, 2011 in U.S. Appl. No. 11/406,794.
Corrected Notice of Allowance dated Jul. 20, 2011 U.S. Appl. No. 11/406,794.
Notice of Allowance dated Oct. 4, 2011 in U.S. Appl. No. 11/406,794.
Notice of Allowance dated Jan. 17, 2012 in U.S. Appl. No. 11/406,794.
Office Action mailed Aug. 17, 2009 in U.S. Appl. No. 11/611,938.
Final Office Action mailed Feb. 25, 2010 in U.S. Appl. No. 11/611,938.
Office Action mailed May 2, 2008 in U.S. Appl. No. 11/611,961.
Final Office Action mailed Jan. 29, 2009 in U.S. Appl. No. 11/611,961.
Notice of Allowance dated Jun. 2, 2009 in U.S. Appl. No. 11/611,961.
Notice of Allowance dated Jan. 6, 2010 in U.S. Appl. No. 11/611,961.
Notice of Allowance dated Apr. 30, 2010 in U.S. Appl. No. 11/611,961.
Notice of Allowance dated Aug. 12, 2010 in U.S. Appl. No. 11/611,961.
Notice of Allowance dated Nov. 30, 2010 in U.S. Appl. No. 11/611,961.
Notice of Allowance dated Mar. 14, 2011 in U.S. Appl. No. 11/611,961.
Notice of Allowance dated Jul. 18, 2011 in U.S. Appl. No. 11/611,961.
Notice of Allowance dated Oct. 26, 2011 in U.S. Appl. No. 11/611,961.
Notice of Allowance dated Feb. 6, 2012 in U.S. Appl. No. 11/611,961.
Office Action mailed Nov. 26, 2008 in U.S. Appl. No. 11/612,071.
Final Office Action mailed Jun. 8, 2009 in U.S. Appl. No. 11/612,071.
Notice of Allowance mailed Oct. 11, 2011 in U.S. Appl. No. 11/612,071.
Final Office Action mailed Aug. 5, 2008 in U.S. Appl. No. 11/612,146.
Final Office Action mailed Oct. 29, 2009 in U.S. Appl. No. 11/612,146.
Office Action mailed Jan. 29, 2009 in U.S. Appl. No. 11/612,174.
Office Action mailed Jul. 11, 2011 in U.S. Appl. No. 12/431,141.
Final Office Action mailed Dec. 15, 2011 in U.S. Appl. No. 12/431,141.
Office Action mailed Mar. 30, 2009 in U.S. Appl. No. 11/612,202.
Office Action mailed Jan. 14, 2010 in U.S. Appl. No. 11/612,202.
Notice of Allowance mailed Jul. 29, 2010 in U.S. Appl. No. 11/612,202.
Notice of Allowance mailed Nov. 15, 2010 in U.S. Appl. No. 11/612,202.
Notice of Allowance mailed Mar. 4, 2011 in U.S. Appl. No. 11/612,202.
Notice of Allowance dated Sep. 19, 2011 in U.S. Appl. No. 11/612,202.
Notice of Allowance mailed Jan. 4, 2012 in U.S. Appl. No. 11/612,202.
Office Action mailed Jul. 9, 2010 in U.S. Appl. No. 11/612,222.
Office Action mailed Apr. 12, 2011 in U.S. Appl. No. 11/612,222.
Final Office Action mailed Oct. 4, 2011 in U.S. Appl. No. 11/612,222.
Office Action mailed Jul. 21, 2009 in U.S. Appl. No. 11/612,249.
Final Office Action mailed Jan. 28, 2010 in U.S. Appl. No. 11/612,249.
Office Action mailed Oct. 15, 2010 in U.S. Appl. No. 11/612,249.
Office Action mailed Apr. 22, 2011 in U.S. Appl. No. 11/612,249.
Office Action mailed Oct. 6, 2011 in U.S. Appl. No. 10/612,249.
Office Action mailed May 21, 2008 in U.S. Appl. No. 11/674,021.
Final Office Action mailed Jul. 31, 2009 in U.S. Appl. No. 11/674,021.
Notice of Allowance mailed Jun. 16, 2010 in U.S. Appl. No. 11/674,021.
Notice of Allowance mailed Dec. 15, 2010 in U.S. Appl. No. 11/674,021.
Notice of Allowance dated Aug. 22, 2011 in U.S. Appl. No. 11/674,021.
Office Action mailed Apr. 29, 2009 in U.S. Appl. No. 11/750,600.
Final Office Action mailed Dec. 16, 2009 in U.S. Appl. No. 11/750,600.
Final Office Action mailed Mar. 11, 2010 in U.S. Appl. No. 11/750,600.
Notice of Allowance mailed May 28, 2010 in U.S. Appl. No. 11/750,600.
Notice of Allowance mailed Dec. 15, 2010 in U.S. Appl. No. 11/750,600.

(56) References Cited

OTHER PUBLICATIONS

Office Action/Interview Summary dated Sep. 1, 2011 in U.S. Appl. No. 11/750,600.
Notice of Allowance dated Sep. 12, 2011 in U.S. Appl. No. 11/750,600.
Notice of Allowance mailed Dec. 22, 2011 in U.S. Appl. No. 11/750,600.
Office Action mailed Jun. 24, 2009 in U.S. Appl. No. 12/055,433.
Final Office Action mailed Feb. 23, 2010 in U.S. Appl. No. 12/055,433.
Office Action mailed Sep. 22, 2010 in U.S. Appl. No. 12/055,433.
Office Action mailed Jun. 8, 2011 in U.S. Appl. No. 12/055,433.
Office Action mailed Dec. 22, 2011 in U.S. Appl. No. 12/055,433.
Office Action mailed May 26, 2011 in U.S. Appl. No. 12/055,695.
Office Action mailed Jul. 15, 2011 in U.S. Appl. No. 12/055,695.
Final Office Action mailed Nov. 21, 2011 in U.S. Appl. No. 12/055,695.
Office Action mailed Nov. 15, 2010 in U.S. Appl. No. 12/055,924.
Notice of Allowance mailed Apr. 12, 2011 in U.S. Appl. No. 12/055,924.
Office Action mailed Oct. 6, 2011 in U.S. Appl. No. 12/349,184.
Office Action mailed Jun. 1, 2010 in U.S. Appl. No. 12/488,079.
Notice of Allowance mailed Dec. 14, 2010 in U.S. Appl. No. 12/488,079.
Notice of Allowance mailed Jun. 21, 2011 in U.S. Appl. No. 12/488,079.
Notice of Allowance dated Nov. 1, 2011 in U.S. Appl. No. 12/488,079.
International Search Report re: PCT/US2009/050745 dated Sep. 22, 2009.
O'Donnell et al., Chapter 15, "Drug Therapy of Depression and Anxiety Disorders", Goodman & Gilman's The Pharmacological Basis of Therapeutics, 12$^{th}$ Edition, 2011, pp. 397-415.
McNamara, J., Chapter 21, "Pharmacotherapy of the Epilepsies", Goodman & Gilman's The Pharmacological Basis of Therapeutics, 12$^{th}$ Edition, 2011, pp. 583-607.
Brodie, M.S.; Pesold, C; Appel, S.B. Alcohol Clin Exp Res 1999, 23, pp. 1848-1852.
Edeh et al, (1987) Relationship between interictal psychopathology and the type of epilepsy. Results of a survey in general practice. Br J Psychiatry 151:95-101.
Ettinger et al., (2004) Depression and comorbidity in community-based patients with epilepsy or asthma. Neurology 63:1008-1014.
Forsgren et al., (1990) An incident case-referent study of epileptic seizures in adults. Epilepsy Res 6:66-81.
Hesdorffer et al. (2006) Depression and suicide attempt as risk factors for incident unprovoked seizures. Ann Neurol 59:35-41.
Hesdorffer et al. (2000) Major depression is a risk factor for seizures in older adults. Ann Neurol 47:246-249.
Jacoby et al. (1996) The clinical course of epilepsy and its psychosocial correlates: findings from a U.K. Community study. Epilepsia 37:148-161.
Kanner, AM., (2006) Epilepsy, suicidal behaviour, and depression: do they share common pathogenic mechanisms? Lancet Neurol 5:107-108.
Krampfl et al., The European Journal of Neuroscience; vol. 22, Issue: 1, pp. 10-20, 2005.
Ottman et al., Epilepsia, 52(2):308-315, 2011.
Scimemi et al., The Journal of Neuroscience: the official journal of Society for Neuroscience; vol. 25; Issue: 43, pp. 10016-10024, 2005.
Wise RA, Drug Alcohol Depend, 1998, 51, pp. 13-22.
Wise RA, NIDA Res Mono, 1984, 50, pp. 15-33.
Notice of Allowance dated Mar. 20, 2012 in U.S. Appl. No. 11/209,122.
Notice of Allowance dated May 10, 2012 in U.S. Appl. No. 11/406,794.
Notice of Allowance dated May 23, 2012 in U.S. Appl. No. 11/611,961.
Notice of Allowance dated Mar. 9, 2012 in U.S. Appl. No. 11/612,071.
Notice of Allowance mailed Apr. 25, 2012 in U.S. Appl. No. 11/612,146.
Interview Summary mailed Mar. 26, 2012 in U.S. Appl. No. 12/431,141.
Notice of Allowance mailed Apr. 16, 2012 in U.S. Appl. No. 11/612,202.
Notice of Allowance dated May 11, 2012 in U.S. Appl. No. 13/301,109.
Office Action mailed Mar. 30, 2012 in U.S. Appl. No. 11/750,600.
Interview Summary mailed Apr. 4, 2012 in U.S. Appl. No. 12/055,433.
Notice of Allowance dated May 11, 2012 in U.S. Appl. No. 12/349,184.
Notice of Allowance mailed Mar. 1, 2012 in U.S. Appl. No. 12/488,079.
Brandt et al., Neuropsychobiology, 1998, 38, pp. 202 to 203.
Dib, Jean G., Current Medical Research and Opinion, 2004, 20, 12, p. 1857-1861.
Keck et al., J. Clin. Psychiatry, 2002, 63 (suppl 4).
Tanimukai et al., International Pharmacopsychiatry, 1970, vol. 5, No. 1, pp. 35 to 43.
Thienel et al., Acta Neurologica Scandinavica, 2004, 110, 4, p. 221-231.
Notice of Allowance dated Jul. 19, 2012 in U.S. Appl. No. 11/154,386.
Notice of Allowance mailed Aug. 27, 2012 in U.S. Appl. No. 11/611,961.
Notice of Allowance mailed Aug. 9, 2012 in U.S. Appl. No. 11/612,202.
Final Office Action mailed Sep. 10, 2012 in U.S. Appl. No. 11/750,600.
Notice of Allowance mailed Jun. 18, 2012 in U.S. Appl. No. 12/488,079.
Notice of Allowance mailed Oct. 10, 2012 in U.S. Appl. No. 12/488,079.
Benjamin et al. J Biomol Screening, 2006, vol. 11, pp. 29-39.
Brown et al. Tetrahedron, 1987, vol. 43, pp. 4071-4078.
Dunham et al. J Am Pharm Assoc Sci Ed, 1957, vol. 46, pp. 208-209.
Ettinger et al. Neurotherapeutics, 2007, vol. 4, pp. 75-83.
Gavernet et al. Bioorg Med Chem 2007, vol. 15, pp. 1556-1567.
Gavernet et al. J Med Chem, 2009, vol. 52, pp. 1592-1601.
Gribkoff, V., Expert Opin Ther Pat., 2003 vol. 7, pp. 737-748.
Kohling, R., Epilepsia, 2002, vol. 43, pp. 1278-1295.
Kuzimski et al., Epilepsia, 2005, vol. 46, pp. 481-489.
Landmark, C., CNS Drugs, 2008, vol. 22, pp. 27-47.
Liu et al., Epilepsy Res, 2006, vol. 70, pp. 263-268.
Liu et al., Neuropharmacology, 2003, vol. 44, pp. 413-422.
Lombardo et al., Mol Brain Res, 1996, vol. 35, pp. 84-90.
Lothman et al., Epilepsy Res, 1988, vol. 2, pp. 356-366.
Lothman et al., Epilepsy Res, 1988, vol. 2, pp. 367-379.
Lukyanetz et al., Epilepsia, 2002, vol. 43, pp. 9-18.
Maryanoff et al, Drugs Future, 1989, vol. 14, pp. 342-344.
Maryanoff et al, J Med Chem, 2008, vol. 51, pp. 2518-2521.
Maryanoff et al., Curr Top Med Chem, 2009, vol. 9, pp. 1049-1062.
Maryanoff, B., J Med Chem, 2009, vol. 52, pp. 3431-3440.
Orloff et al., Proc Soc Exp Biol Med, 1949, vol. 70, pp. 254-257.
Parker et al., J Med Chem, 2009, vol. 52, pp. 7528-7536.
Remington's The Science and Practice of Pharmacy, 19th Edition, Published 1998, vol. I, pp. 371-375.
Remington's The Science and Practice of Pharmacy, 19th Edition, Published 1998, vol. II, pp. 2226-2241 [see attached translation as provided from foreign agent in Colombia, detailing only portions of the article as cited by the Colombian examiner containing indications regarding the general procedures for manufacturing, isolating and purifying crystals and polymorphs].
Rogawski et al., Nat Med, 2004, vol. 10, pp. 685-692.
Rogawski, M., Epilepsy Res, 2006, vol. 69, pp. 273-294.
Shank et al., CNS Neurosci Ther, 2008, vol. 14, pp. 120-142.
Shank et al., Epilepsia, 1994, vol. 35, pp. 450-460.
Shank et al., J Enzym INH Med Chem, 2008, vol. 23, pp. 271-276.
Shingles et al., Anal Biochem, 1997, vol. 252, pp. 190-197.
Stella et al., Drugs, 29: 455-473 (1985).
Soderpalm, B., Eur J Pain, 2002, vol. 6, Suppl A, p. 3-9.

(56) References Cited

OTHER PUBLICATIONS

Swinyard et al., J Pharmacol Exp Ther, 1952, vol. 106, pp. 319-330.
Swinyard, E., Epilepsia, 1969, vol. 10, pp. 107-119.
Wang et al., Science, 1998 vol. 282, pp. 1890-1893.
White et al., Antiepileptic Drugs, 5th Ed., 2002, pp. 36-48.
White et al., Epilepsy Res, 1992, vol. 12, pp. 217-226.
White et al., Int Rev Neurobiol, 2007, vol. 81, pp. 85-110.
Winum et al., Expert Opin Ther Pat, 2006, vol. 16, pp. 27-47.
Zaremba et al., Pharmacol Rep, 2006, vol. 58, pp. 1-12.
Loscher, et al., Pharma. Rev., 62, 668-700 (2010).
Walker, et al., Brain, 125, 1937-1950 (2002).
McNamara et al. Analyses of the molecular basis of kindling development. Psychiatry and Clinical Neurosciences, 1995, 49, S175-S178.
Loscher et al. Antiepileptogenic effects of the novel anticonvulsant levetiracetam (ucb L059) in the kindling model of temporal lobe epilepsy. The Journal of Pharmacology and Experimental Therapeutics, vol. 284, No. 2, 1998, pp. 474-479.
Notice of Allowance dated Nov. 20, 2012 in U.S. Appl. No. 11/154,386.
Notice of Allowance dated May 8, 2013 in U.S. Appl. No. 11/154,386.
Notice of Allowance dated May 10, 2013 in U.S. Appl. No. 11/209,122.
Notice of Allowance mailed Dec. 24, 2012 in U.S. Appl. No. 11/611,938.
Notice of Allowance mailed Mar. 27, 2013 in U.S. Appl. No. 11/611,938.
Notice of Allowance dated Dec. 10, 2012 in U.S. Appl. No. 11/611,961.
Notice of Allowance dated Apr. 2, 2013 in U.S. Appl. No. 11/611,961.
Notice of Allowance mailed Jan. 22, 2013 in U.S. Appl. No. 11/612,071.
Notice of Allowance mailed Jul. 8, 2013 in U.S. Appl. No. 11/612,071.
Office Action mailed Jul. 19, 2013 in U.S. Appl. No. 12/431,141.
Notice of Allowance mailed Nov. 26, 2012 in U.S. Appl. No. 11/612,202.
Notice of Allowance mailed Mar. 18, 2013 in U.S. Appl. No. 11/612,202.
Notice of Allowance mailed Jul. 9, 2013 in U.S. Appl. No. 11/612,202.
Office Action mailed Mar. 14, 2013 in U.S. Appl. No. 11/750,600.
Office Action mailed May 23, 2013 in U.S. Appl. No. 12/055,433.
Notice of Allowance mailed Feb. 7, 2013 in U.S. Appl. No. 12/488,079.
Notice of Allowance mailed Mar. 27, 2013 in U.S. Appl. No. 12/488,079.
Amano K, Hamada K, Yagi K, Seino M. Antiepileptic effects of topiramate on amygdaloid kindling in rats. Epilepsy Res. Jul. 1998; 31(2):123-8.
Barton ME, White HS. The effect of CGX-1007 and CI-1041, novel NMDA receptor antagonists, on kindling acquisition and expression. Epilepsy Res. Mar. 2004; 59(1):1-12.
Chengappa et al., "Topiramate as add-on treatment for patients with bipolar mania" in Bipolar Disorders, vol. 1, Issue 1, 42-53, Sep. 1999), Abstract attached.
Kinrys, G et al. Levetiracetam as Adjunctive Therapy for Refractory Anxiety Disorders. J. Clin. Psychiatry 68; Jul. 7, 2007: 1010-1013.
Kinrys, G et al. Levetiracetam or Treatment-Refractory Post-traumatic Stress Disorder J. Clin. Psychiatry 67: Feb 2, 2006: 211-214.
Morimoto K, Katayama K, Inoue K, Sato K. Effects of competitive and noncompetitive NMDA receptor antagonists on kindling and LTP. Pharmacol Biochem Behav. Dec. 1991; 40(4):893-9.
Mula et al. ("Psycopharmacology of topiramate: from epilepsy to bipolar disorder" in Neuropsychiatric Disease and Treatment 2006:2(4) 475-488).
Nowack et al., Am J Physiol Cell Physiol, 299: C960-C967, 2010.
Otagiri et al., "PRODRUG in "The New Drug Delivery System" (2000), CMC Publishing Co., Ltd., pp. 123-135 [translation of extracted portions from p. 124—subsection 2.2 Design of Prodrugs" and Table 1].
Racine, R.J. 1972. Modification of seizure activity by electrical stimulation. II. Motor seizure. Electroencephalogr. Clin. Neurophysiol. 32, 281-294.
Zhang, W et al. Levetiracetam in social phobia: a placebo controlled pilot study. J. Psychopharm. 19(5) (2005) 551-553.
Notice of Allowance dated Aug. 29, 2013 in U.S. Appl. No. 11/154,386.
Notice of Allowance dated Dec. 16, 2013 in U.S. Appl. No. 11/154,386.
Notice of Allowance dated Sep. 16, 2013 in U.S. Appl. No. 11/209,122.
Notice of Allowance dated Feb. 20, 2014 in U.S. Appl. No. 11/209,122.
Notice of Allowance dated Dec. 20, 2013 in U.S. Appl. No. 11/612,071.
Notice of Allowance dated Sep. 23, 2013 in U.S. Appl. No. 11/612,146.
Final Office Action mailed Dec. 30, 2013 in U.S. Appl. No. 12/431,141.
Notice of Allowance dated Jul. 9, 2013 in U.S. Appl. No. 11/612,202.
Notice of Allowance dated Oct. 25, 2013 in U.S. Appl. No. 11/612,202.
Final Office Action mailed Aug. 6, 2013 in U.S. Appl. No. 11/612,222.
Final Office Action mailed Jan. 16, 2014 in U.S. Appl. No. 11/612,222.
Final Office Action mailed Feb. 4, 2014 in U.S. Appl. No. 11/612,249.
Notice of Allowance dated Oct. 16, 2013 in U.S. Appl. No. 13/301,109.
Office Action mailed Feb. 25, 2014 in U.S. Appl. No. 11/750,600.
Final Office Action mailed Nov. 14, 2013 in U.S. Appl. No. 12/055,433.
Notice of Allowance dated Aug. 9, 2013 in U.S. Appl. No. 12/488,079.
Notice of Allowance dated Nov. 8, 2013 in U.S. Appl. No. 12/488,079.

\* cited by examiner

SUBSTITUTED SULFAMIDE DERIVATIVES

CROSS REFERENCE TO RELATED APPLICATIONS

This application claims the benefit of U.S. Provisional Application 61/082,654, filed on Jul. 22, 2008, which is incorporated by reference herein in its entirety.

FIELD OF THE INVENTION

The present invention is directed to novel substituted sulfamide derivatives, pharmaceutical compositions containing said derivatives and the use of said derivatives form in the treatment of anxiety and related disorders; bipolar depression and mania; depression; epilepsy and related disorders; epileptogenesis; glucose related disorders; lipid related disorders; migraine; obesity; pain; substance abuse and as neuroprotective agents. The present invention is further directed to a process for the preparation of the novel substituted sulfamide derivatives.

BACKGROUND OF THE INVENTION

US Patent Publication US2006-0041008 A1, published Feb. 23, 2006 discloses benzo-fused sulfamide derivatives useful for the treatment of epilepsy and related disorders; US Patent Publication 2007-0293441 A1, published Nov. 18, 2008 discloses co-therapy for the treatment of epilepsy and related disorder comprising administration of benzo-fused sulfamide derivatives and on or more anticonvulsants and/or anti-epileptic agents; US Patent Publication US2007-0155826 A1, published Jul. 5, 2007 discloses the use of benzo-fused sulfamide derivatives for the treatment of bipolar disorder and mania; US Patent Publication US2007-0155827 A1, published Jul. 5, 2007 discloses the use of benzo-fused sulfamide derivatives for the treatment of depression; US Patent Publication US2007-0155824 A1, published Jul. 5, 2007 discloses the use of benzo-fused sulfamide derivatives for the treatment of epileptogenesis; US Patent Publication US2007-0155821 A1, published Jul. 5, 2007 discloses the use of benzo-fused sulfamide derivatives for the treatment of glucose related disorders and for the treatment of lipid related disorders; US Patent Publication US2007-0191474 A1, published Aug. 16, 2007 discloses the use of benzo-fused sulfamide derivatives for the treatment of migraine; US Patent Publication US2007-015823 A1, published Jul. 5, 2007 discloses the use of benzo-fused sulfamide derivatives for neuroprotection; US Patent Publication US2008-0027131 A1, published Jan. 31, 2008 discloses the use of benzo-fused sulfamide derivatives for the treatment of obesity; US Patent Publication US2007-0155822 A1, published Jul. 5, 2007 discloses the use of benzo-fused sulfamide derivatives for the treatment of pain; US Patent Publication US2007-0155825 A1, published Jul. 5, 2007 discloses the use of benzo-fused sulfamide derivatives for the treatment of substance abuse and/or addiction; which are herein incorporated by reference in their entirety.

SUMMARY OF THE INVENTION

The present invention is directed to compounds of formula (I)

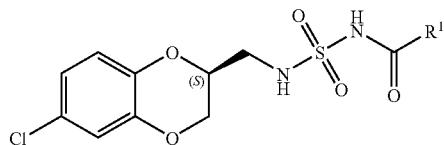

(I)

wherein
R$^1$ is selected from the group consisting of C$_{1-4}$alkyl and —O-phenyl; wherein the phenyl is optionally substituted with one to three substituents, independently selected from the group consisting of halogen, C$_{1-4}$alkyl, fluorinated C$_{1-4}$alkyl, C$_{1-4}$alkoxy, fluorinated C$_{1-4}$alkoxy, cyano, nitro, —NR$^A$R$^B$ and —C(O)—NR$^C$R$^D$; wherein R$^A$ and R$^B$ are each independently selected from the group consisting of C$_{1-4}$alkyl; and wherein R$^D$ and R$^D$ are each independently selected from the group consisting of hydrogen and C$_{1-4}$alkyl;
and pharmaceutically acceptable salts thereof;
provided that when R$^1$ is methyl, then the compound of formula (I) is present as an isolated or substantially pure form.

The present invention is further directed to an acetyl-substituted sulfamide derivative, a compound of formula (A)

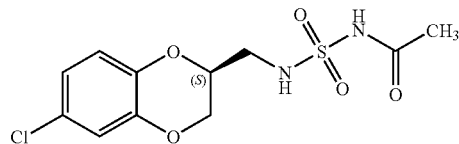

(A)

and pharmaceutically acceptable salts thereof; also known as (2S)-(−)-N'-acetyl-N-(6-chloro-2,3-dihydro-benzo[1,4]dioxin-2-ylmethyl)-sulfamide; wherein the compound of formula (A) is present as an isolated or substantially pure form; preferably the compound of formula (A) is present as an isolated and substantially pure form.

The present invention is further directed to a process for the preparation of compounds of formula (I), as described in more detail herein. In an embodiment, the present invention is directed to a process for the preparation of a compound of formula (A), as described in more detail herein. The present invention is further directed to a product prepared according to any of the processes described herein.

Illustrative of the invention is a pharmaceutical composition comprising a pharmaceutically acceptable carrier and a compound of formula (I), preferably a compound of formula (A). An illustration of the invention is a pharmaceutical composition made by mixing a compound of formula (I), preferably a compound of formula (A) and a pharmaceutically acceptable carrier. Illustrating the invention is a process for making a pharmaceutical composition comprising mixing a compound of formula (I), preferably a compound of formula (A) and a pharmaceutically acceptable carrier.

The present invention is further directed to methods for the treatment of anxiety and related disorders; bipolar depression and mania; depression; epilepsy and related disorders; epileptogenesis; glucose related disorders; lipid related disorders; migraine; obesity; pain; substance abuse or neuroprotection comprising administering to a subject in need thereof a therapeutically effective amount of the compound of formula (I), preferably a compound of formula (A).

Another example of the invention is the use of the compound of formula (I), preferably a compound of formula (A)

in the preparation of a medicament for treating: (a) anxiety and related disorders; (b) bipolar depression (c) mania; (d) depression; (e) epilepsy and related disorders; (f) epileptogenesis; (g) glucose related disorders; (h) lipid related disorders; (i) migraine; (j) obesity; (k) pain; (l) substance abuse and (m) for neuroprotection, in a subject in need thereof.

DETAILED DESCRIPTION OF THE INVENTION

The present invention is directed to compounds of formula (I)

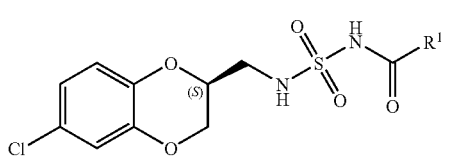

wherein $R^1$ is as herein defined; and pharmaceutically acceptable salts thereof; useful as prodrugs of the compound of formula (S)

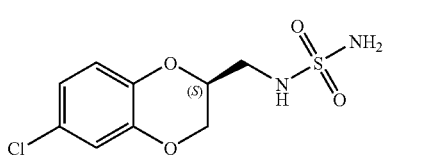

also known as (2S)-(−)-N-(6-chloro-2,3-dihydro-benzo[1,4]dioxin-2-ylmethyl)-sulfamide (disclosed in US Patent Publication US2006-0041008 A1, published Feb. 23, 2006). In an embodiment, the present invention is directed to an acetyl-substituted sulfamide derivative, a compound of formula (A)

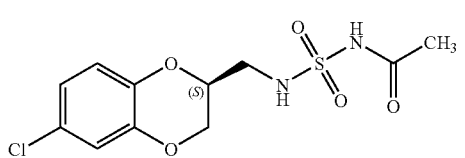

and pharmaceutically acceptable salts thereof. The compound of formula (A) is a human metabolite of the compound of formula (S)

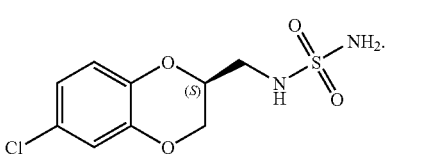

The compound of formula (A) was initially isolated from human plasma samples from clinical trials dosing with the compound of formula (S). Additionally, the compound of formula (A) is a pro-drug of the compound of formula (S). In mice studies dosing with the compound of formula (A), plasma and brain analyses showed the presence of both the compound of formula (A) and the compound of formula (S), with the levels of the compound of formula (S) higher than those of the compound of formula (A).

The present invention is further directed to the use of compounds of formula (I), preferably the compound of formula (A), for the treatment of anxiety and related disorders; bipolar depression and mania; depression; epilepsy and related disorders; epileptogenesis; glucose related disorders; lipid related disorders; migraine; obesity; pain; substance abuse and for neuroprotection.

The present invention is further directed to pharmaceutical compositions comprising a compound of formula (I), preferably a compound of formula (A).

In an embodiment of the present invention, $R^1$ is selected from the group consisting of $C_{1-4}$alkyl. In another embodiment of the present invention, $R^1$ is selected from the group consisting of $C_{2-4}$alkyl and —O-phenyl. In another embodiment of the present invention, $R^1$ is selected from the group consisting of $C_{2-4}$alkyl. In another embodiment of the present invention, $R^1$ is selected from the group consisting of methyl, ethyl and t-butyl. In yet another embodiment of the present invention, $R^1$ is methyl.

In an embodiment of the present invention, $R^1$ is selected from the group consisting of —O-phenyl; wherein the phenyl is optionally substituted with one to three substituents (preferably one to two substituents, more preferably one substituent), independently selected from the group consisting of halogen, $C_{1-4}$alkyl, fluorinated $C_{1-4}$alkyl, $C_{1-4}$alkoxy, fluorinated $C_{1-4}$alkoxy, cyano, nitro, —$NR^AR^B$ and —C(O)—$NR^CR^D$; wherein $R^A$ and $R^B$ are each independently selected from the group consisting of $C_{1-4}$alkyl; and wherein $R^C$ and $R^D$ are each independently selected from the group consisting of hydrogen and $C_{1-4}$alkyl. In another embodiment of the present invention, $R^1$ is selected from the group consisting of —O-phenyl; wherein the phenyl is optionally substituted with a substituent selected from the group consisting of halogen, $C_{1-4}$alkyl, —$CF_3$, $C_{1-4}$alkoxy, —$OCF_3$, cyano, nitro, —$NR^AR^B$ and —C(O)—$NR^CR^D$.

In an embodiment of the present invention, $R^A$ and $R^B$ are each independently selected from the group consisting of methyl, ethyl and t-butyl. In another embodiment of the present invention, $R^C$ and $R^D$ are each independently selected from the group consisting of hydrogen, methyl, ethyl and t-butyl.

As used herein, "halogen" shall mean chlorine, bromine, fluorine and iodine. Preferably, the halogen is chlorine or fluorine.

As used herein, the term "$C_{1-4}$alkyl" whether used alone or as part of a substituent group, shall include straight and branched chains containing one to four carbon atoms. For example, alkyl radicals include methyl, ethyl, n-propyl, iso-propyl, n-butyl, isobutyl, sec-butyl and t-butyl.

As used herein, unless otherwise noted, the term "fluorinated $C_{1-4}$alkyl" shall mean any $C_{1-4}$alkyl group as defined above substituted with at least one fluoro atom. Suitable examples include but are not limited to —$CH_2F$, —$CF_3$, —$CH_2$—$CF_3$, —$CF_2$—$CF_2$—$CF_2$—$CF_3$, and the like.

As used herein, unless otherwise noted, "$C_{1-4}$alkoxy" shall denote an oxygen ether radical of any the above described straight or branched chain alkyl groups containing one to four carbon atoms. For example, methoxy, ethoxy, n-propoxy, iso-propoxy, n-butoxy, sec-butoxy and, t-butoxy.

As used herein, unless otherwise noted, the term "fluorinated $C_{1-4}$alkoxy" shall mean any $C_{1-4}$alkoxy group as defined above substituted with at least one fluoro atom. Suitable examples include but are not limited to —$OCH_2F$, —$OCF_3$, —$OCH_2$—$CF_3$, —$OCF_2$—$CF_2$—$CF_2$—$CF_3$, and the like.

Where the compound according to this invention has at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%.

As used herein, unless otherwise noted, the term "isolated form" shall mean that the compound is present in a form which is separate from any biological environment (e.g. plasma, blood, gastric fluids, urine, cerebrospinal fluid, and the like). In an embodiment of the present invention, the compound of formula (I), preferably, the compound of formula (A) is present as an isolated form.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, the compound of formula (I), preferably, the compound of formula (A) is a substantially pure form.

As used herein, unless otherwise noted, the term "substantially free of corresponding salt form(s)" when used to described the compound of formula (I), preferably a compound of formula (A) shall mean that mole percent of salt forms of the compound of formula (I), preferably a compound of formula (A) is less than about 5 mole percent, preferably less than about 2 mole percent, more preferably, less than about 0.5 mole percent, most preferably less than about 0.1 mole percent. In an embodiment of the present invention, the compound of formula (I), preferably, the compound of formula (A) is substantially free of corresponding salt form(s).

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

As used herein, the terms "anxiety and related disorders" and "anxiety or a related disorder" shall be defined to include anxiety and related disorders including generalized anxiety disorder, acute stress disorder, post traumatic stress disorder, obsessive-compulsive disorder, social phobia (also known as social anxiety disorder), specific phobia, panic disorder with or without agoraphobia, agoraphobia without a history of panic disorder, anxiety disorder due to general medical condition, substance abuse induced anxiety disorder and anxiety disorder not otherwise specified (as these conditions are described by their diagnostic criteria, as listed in the *Diagnostic and Statistical Manual of Mental Disorders*, 4$^{th}$ Edition, Text Revision, American Psychiatric Association, 2000, incorporated herein by reference). Preferably, the anxiety or related disorder is selected from the group consisting of generalized anxiety disorder, acute stress disorder, post traumatic stress disorder and obsessive-compulsive disorder. More preferably, the anxiety and related disorder is generalized anxiety disorder.

Bipolar disorder is psychiatric disorder characterized by unpredictable swings in mood from mania (or hypomania) to depression. As used herein, the term "bipolar disorder" shall include bipolar disorder I, bipolar disorder II, cyclothymic disorder and bipolar disorder not otherwise specified. Preferably, the bipolar disorder is characterized by depressive and manic (or hypomanic) phases, wherein the phases cycle. Preferably, the bipolar disorder is bipolar disorder I or bipolar disorder II.

As used herein, the term "bipolar depression" is intended to mean the depression associated with, characteristic of or symptomatic of a bipolar disorder. Thus, methods of treating bipolar depression of the present invention are directed to methods which treat the depression and/or depressed phase of bipolar disorders.

As used herein, unless otherwise noted the terms "cycling" or "bipolar cycling" shall refer to the alternation of mood between depressive and manic phases characteristic of bipolar disorders. Thus, the present invention includes methods for the stabilization of said cycling, including, but not limited to, decreasing the frequency of the cycling and/or decreasing the magnitude of the manic and/or depressive phases.

As used herein, the term "mania" shall include mania or a manic mood phase, regardless of underlying cause. As used herein, the term "bipolar mania" is intended to mean the mania associated with, characteristic of or symptomatic of a bipolar disorder. Thus, methods of treating bipolar mania of the present invention are directed to methods which treat the mania and/or manic phase of bipolar disorders.

As used herein, the term "depression" shall be defined to include major depressive disorder (including single episode and recurrent), unipolar depression, treatment-refractory depression, resistant depression, anxious depression and dysthymia (also referred to as dysthymic disorder). Further, the term "depression" shall encompass any major depressive disorder, dysthymic disorder and depressive disorder not otherwise specific as defined by their diagnostic criteria, as listed in the *Diagnostic and Statistical Manual of Mental Disorders*, 4$^{th}$ Edition, Text Revision, American Psychiatric Association, 2000. Preferably, the depression is major depressive disorder, unipolar depression, treatment-refractory depression, resistant depression or anxious depression. More preferably, the depression is major depressive disorder.

As used herein, unless otherwise noted, the terms "epilepsy and related disorders" or "epilepsy or related disorder" shall mean any disorder in which a subject (preferably a human adult, child or infant) experiences one or more seizures and/or tremors. Suitable examples include, but are not limited to, epilepsy (including, but not limited to, localization-related epilepsies, generalized epilepsies, epilepsies with both generalized and local seizures, and the like), seizures as a complication of a disease or condition (such as seizures associated with encephalopathy, phenylketonuria, juvenile Gaucher's disease, Lundborg's progressive myoclonic epilepsy, stroke, head trauma, stress, hormonal changes, drug use or withdrawal, alcohol use or withdrawal, sleep deprivation, and the like), essential tremor, restless limb syndrome, and the like. Preferably, the disorder is selected from epilepsy (regardless of type, underlying cause or origin), essential tremor or restless limb syndrome, more preferably, the disorder is epilepsy (regardless of type, underlying cause or origin) or essential tremor.

As used herein, the term "epileptogenesis" shall mean the biochemical, genetic, histological or other structural or functional processes or changes that make nervous tissue, including the central nervous system (CNS) susceptible to recurrent, spontaneous seizures. In addition, the term "epileptogenesis" is also used herein in a broader sense to refer to the changes and/or processes that contribute to the clinical progression observed in patients with epilepsy or other seizure disorder or an analogous seizure-related disorder including but not limited to; the worsening or progression of the disorder and it's symptoms or the development of "pharmacoresistance," in which the disorder becomes more difficult to treat as a result of neurobiological changes which result in reduced drug sensitivity or the recruitment by the process of epileptogenesis of non seizure prone nervous tissue. Furthermore the term "epileptogenesis" is used herein in the broadest possible sense to refer to the similar phenomena of progressive worsening over time of the signs and symptoms of apparently non-epileptic disorders, including psychiatric disorders the etiology of which appear to be seizure related.

Epileptogenesis is a Two Phase Process: "Phase 1 epileptogenesis" is the initiation of the epileptogenic process prior to the first epileptic seizure or symptom of an analogous seizure-related disorder, and is often the result of some kind of injury or trauma to the brain, i.e., stroke, disease (e.g., infection such as meningitis), or trauma, such as an accidental blow to the head or a surgical procedure performed on the brain. "Phase 2 epileptogenesis" refers to the process during which brain tissue that is already susceptible to epileptic seizures or seizure related phenomena of an analogous seizure-related disorder, becomes still more susceptible to seizures of increasing frequency and/or severity and/or becomes less responsive to treatment.

As used herein, the term "glucose related disorder" shall be defined as any disorder which is characterized by elevated glucose levels. Glucose related disorders include elevated glucose level, pre-diabetes, impaired oral glucose tolerance, poor glycemic control, Type II Diabetes Mellitus, Syndrome X (also known as metabolic syndrome), gestational diabetes, insulin resistance, hyperglycemia and loss of muscle mass as a results of hyperglycemia (cachexia).

Treatment of glucose related disorders may comprise lowering glucose levels, improving glycemic control, decreasing insulin resistance and/or preventing the development of a glucose related disorder (for example preventing a patient suffering from impaired oral glucose tolerance or elevated glucose levels from developing Type II diabetes mellitus).

As used herein, the term "lipid related disorder" shall be defined as any disorder which is characterized by non-normal lipid levels. Lipid related disorders include elevated triglyceride levels, low HDL cholesterol and dyslipidemia, preferably elevated triglyceride levels or low HDL cholesterol levels Treatment of lipid related disorder may comprise lowering triglycerides, elevating HDL cholesterol and/or improving the triglyceride/HDL ratio.

As used herein, the term "migraine" shall mean a chronic, episodic and debilitating clinical condition that is diagnosed by the presence of moderate to severe pulsating unilateral headaches lasting between 4 and 72 h, which includes migraine without aura and migraine with aura.

As used herein, "migraine without aura" shall mean at least five attacks fulfilling the following criteria: (a) the headache attack lasts 4-72 hours with the headache having at least two of the following features: unilateral location, pulsating quality, moderate or severe intensity with direct influence on activities of daily living, and aggravation by walking up stairs or similar routines; and (b) during the headache at least one of the following occurs: nausea and/or vomiting, and photophobia and phonophobia.

As used herein, "migraine with aura" shall mean at least two attacks accompanied by at least 3 of the 4 following features: (a) one or more fully reversible aura symptoms; (b) at least one aura symptom which develops gradually over more than four minutes or two or more symptoms which occur in succession; (c) no aura symptom which lasts more than 60 minutes; (d) a headache occurs prior to, simultaneously with or following the aura, with a free interval between aura and headache of less than about 60 minutes.

As used herein, the term "prevention" shall include the prevention of migraine attacks (headaches), a decrease in the frequency of migraine attacks (headaches), a decrease in the severity of migraine attacks (headaches) and/or a decrease in the duration of migraine attacks (headaches).

As used herein, the term "obesity" shall be defined as a body mass index (BMI) of greater than or equal to about 25, preferably a BMI of greater than or equal to about 30. Thus as used herein, the term "obesity" shall include both overweight and clinically obese subjects/patients.

As used herein, the term "pain" shall be defined to include acute, chronic, inflammatory and neuropathic pain (preferably diabetic neuropathy). Further, the pain may be centrally mediated, peripherally mediated, caused by structural tissue injury, caused by soft tissue injury or caused by progressive disease. Any centrally mediated, peripherally mediated, structural tissue injury, soft tissue injury or progressive disease related pain may be acute or chronic.

As used herein, unless otherwise noted, pain shall include inflammatory pain, centrally mediated pain, peripherally mediated pain, visceral pain, structural related pain, cancer pain, soft tissue injury related pain, progressive disease related pain, neuropathic pain, acute pain from acute injury, acute pain from trauma, acute pain from surgery, headache, dental pain, back pain (preferably lower back pain), chronic pain from neuropathic conditions and chronic pain from post-stroke conditions.

In an embodiment of the present invention, is a method for the treatment of pain, wherein the pain is acute pain. In another embodiment of the present invention, is a method for the treatment of pain, wherein the pain is chronic pain. In another embodiment of the present invention, is a method for the treatment of pain, wherein the pain is neuropathic pain, more preferably diabetic neuropathy. In yet another embodiment of the present invention, is a method for the treatment of pain, wherein the pain is inflammatory pain.

In an embodiment, the pain is selected from the group consisting of osteoarthritis, rheumatoid arthritis, fibromyalgia, headache, toothache, burn, sunburn, animal bite (such as dog bite, cat bite, snake bite, spider bite, insect sting, and the like), neurogenic bladder, benign prostatic hypertrophy, interstitial cystitis, rhinitis, contact dermatitis/hypersensitivity, itch, eczema, pharyngitis, mucositis, enteritis, cellulites, causalgia, sciatic neuritis, mandibular joint neuralgia, peripheral neuritis, polyneuritis, stump pain, phantom limb pain, post-operative ileus, cholecystitis, postmastectomy pain syndrome, oral neuropathic pain, Charcot's pain, reflex sympathetic dystrophy, Guillain-Barre syndrome, meralgia paresthetica, burning-mouth syndrome, post-herpetic neuralgia, trigeminal neuralgia, peripheral neuropathy, bilateral peripheral neuropathy, diabetic neuropathy, postherpetic neuralgia, trigeminal neuralgia, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, inflammatory bowel disease, irritable bowel syndrome, labor, childbirth, menstrual cramps, cancer, back pain, lower back pain and carpal tunnel syndrome pain.

Acute pain includes pain caused by acute injury, trauma, illness or surgery (for example, open-chest surgery (including open-heart or bypass surgery)). Acute pain also includes, and is not limited to, headache, post-operative pain, kidney stone pain, gallbladder pain, gallstone pain, obstetric pain, rheumatological pain, dental pain or pain caused by sports-medicine injuries, carpal tunnel syndrome, burns, musculoskeletal sprains and strains, musculotendinous strain, cervicobrachial pain syndromes, dyspepsia, gastric ulcer, duodenal ulcer, dysmenorrhea or endometriosis.

Chronic pain includes pain caused by an inflammatory condition, osteoarthritis, rheumatoid arthritis or as sequela to disease, acute injury or trauma. Chronic pain also includes, and is not limited to, headache, upper back pain or lower back pain (selected from back pain resulting from systematic, regional or primary spine disease (selected from radiculopathy)), bone pain (selected from bone pain due to osteoarthritis, osteoporosis, bone metastases or unknown reasons), pelvic pain, spinal cord injury-associated pain, cardiac chest pain, non-cardiac chest pain, central post-stroke pain, myofascial pain, cancer pain, AIDS pain, sickle cell pain, geriatric pain or pain caused by headache, migraine, trigeminal neuralgia, temporomandibular joint syndrome, fibromyalgia syndrome, osteoarthritis, rheumatoid arthritis, gout, fibrositis or thoracic outlet syndromes.

Neuropathic pain includes pain resulting from chronic or debilitating conditions or disorders. The chronic or debilitating conditions or disorders which can lead to neuropathic pain include, but are not limited to, painful diabetic peripheral neuropathy, post-herpetic neuralgia, trigeminal neuralgia, post-stroke pain, multiple sclerosis-associated pain, neuropathies-associated pain such as in idiopathic or post-traumatic neuropathy and mononeuritis, HIV-associated neuropathic pain, cancer-associated neuropathic pain, carpal tunnel-associated neuropathic pain, spinal cord injury-associated pain, complex regional pain syndrome, fibromyalgia-associated neuropathic pain, lumbar and cervical pain, reflex sympathic dystrophy, phantom limb syndrome and other chronic and debilitating condition-associated pain syndromes.

As used herein, the term "treatment of substance abuse" shall include treatment of substance abuse or addiction, including but not limited to the treatment of carvings, withdrawal, and other symptoms of addiction or abuse. As used herein, unless otherwise noted the term "substance" when referring to substances of abuse and/or addiction shall include any legal or illegal substance to which a subject or patient may develop an addiction. Suitable examples include, but are not limited to alcohol, cocaine, heroine, methamphetamine, ketamine, Ecstacy, nicotine, oxycontin/oxycodone, codeine, morphine, and the like.

As used herein, the term "neuroprotection" shall mean the protecting neurons in the brain, central nervous system or peripheral nervous system (preferably in the brain or spinal cord) from death and/or damage. Preferably, the neurons are protected from death or damage caused by oxidative stress, for example oxygen radicals.

"Acute neurodegenerative disorders" included within the methods of the present invention include, but are not limited, to various types of acute neurodegenerative disorders associated with neuron death or damage including cerebrovascular insufficiency, focal brain trauma, diffuse brain damage, and spinal cord injury, that is, cerebral ischemia or infarction including embolic occlusion and thrombotic occlusion, repperfusion following acute ischemia, perinatal hypoxic-ischemic injury, cardiac arrest, as well as intracranial hemorrhage of any type (including, but not limited to, epidural, subdural, subarachnoid and intracerebral), and intracranial and intravertebral lesions (including, but not limited to, contusion, penetration, shear, compression and laceration), and whiplash shaken infant syndrome. Preferably, the acute neurodegenerative disorder is a result of stroke, acute ischemic injury, head injury or spinal injury.

"Chronic neurodegenerative disorders" included within the methods of the present invention included, but are not limited to, Alzheimer's disease, Pick's disease, diffuse Lewy body disease, progressive supranuclear palsy (Steel-Richardson syndrome), multisystem degeneration (Shy-Drager syndrome), chronic epileptic conditions associated with neurodegeneration, motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies (including multiple system atrophy), primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), multiple sclerosis, primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, familial dysautonomia (Riley-Day syndrome), and prion diseases (including, but not limited to Creutzfeldt-Jakob, Gerstmann-Straussler-Scheinker disease, Kuru and fatal familial insomnia). Preferably, the chronic neurodegenerative disorder is selected from Alzheimer's disease, Parkinson's disease, multiple sclerosis or cerebral palsy, Other disorders which manifest neuron death or damage and as such are intended to be included within the methods of the present invention include dementias, regardless of underlying etiology, including age-related dementia and other dementias and conditions with memory loss including dementia associated with Alzheimer's disease, vascular dementia, diffuse white matter disease (Binswanger's disease), dementia of endocrine or metabolic origin, dementia of head trauma and diffuse brain damage, dementia pugilistica and frontal lobe dementia.

Also included within the present invention are methods of neuroprotection (i.e. methods for the prevention of neuron death and/or damage) following injury to the brain, central nervous system or peripheral nervous system, wherein the injury resulting from chemical, toxic, infectious, radiation and/or traumatic injury. Preferably, the methods of the present invention are directed to preventing neuron death or damage following brain, head and/or spinal cord trauma or injury, regardless of cause.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

One skilled in the art will recognize that, where not otherwise specified, the reaction step(s) is performed under suitable conditions, according to known methods, to provide the desired product. One skilled in the art will further recognize that wherein a reaction step of the present invention may be carried out in a variety of solvents or solvent systems, said reaction step may also be carried out in a mixture of the suitable solvents or solvent systems.

One skilled in the art will recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

As used herein, unless otherwise noted, the term "leaving group" shall mean a charged or uncharged atom or group which departs during a substitution or displacement reaction.

Suitable examples include, but are not limited to, Br, Cl, I, acetoxy, phenoxy, and the like.

Compounds of formula (I) may be prepared according to the process outlined in Scheme 1.

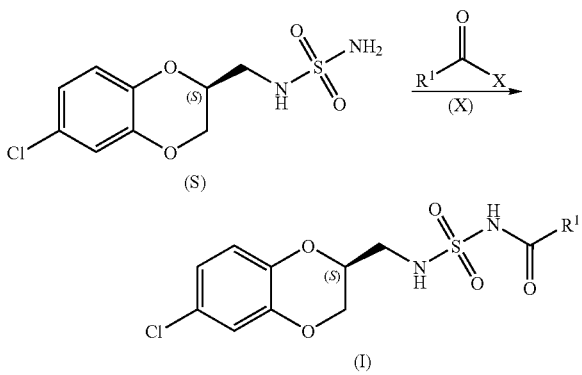

Accordingly, a compound of formula (S) is reacted with a suitably substituted compound of formula (X), a known compound or compound prepared by known methods, wherein X is a suitably selected leaving group such as Br, Cl, I, acetoxy, phenyloxy, and the like, preferably X is Cl; a known compound or compound prepared by known methods;

in an organic solvent such as THF, 1,4-dioxane, chloroform and the like; preferably at a temperature in the range of from about 60° C. to about 100° C., for example, at about solvent reflux temperature; to yield the corresponding compound of formula (I).

In an embodiment, the compound of formula (A) may be prepared as outlined in Scheme 2, below.

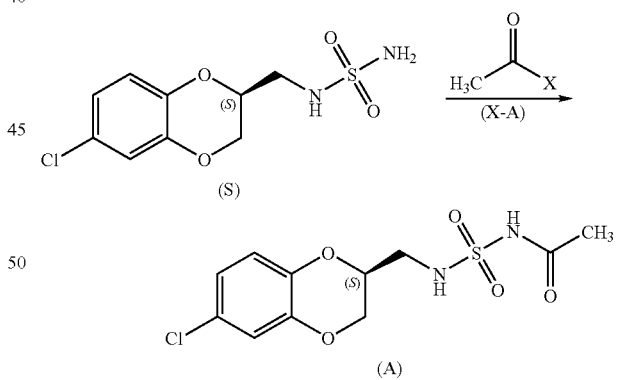

Accordingly, a compound of formula (S) is reacted with a suitably substituted compound of formula (X-A), a known compound or compound prepared by known methods, wherein X is a suitably selected leaving group such as Br, Cl, I, acetoxy, phenyloxy, and the like, preferably X is Cl; a known compound or compound prepared by known methods;

in an organic solvent such as THF, 1,4-dioxane, chloroform and the like; preferably at a temperature in the range of from about 60° C. to about 100° C., for example, at about solvent reflux temperature; to yield the corresponding compound of formula (A).

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention further comprises pharmaceutical compositions containing a compound of formula (I) (for example the compound of formula (A)), with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1-1000 mg or any range therein, and may be given at a dosage of from about 0.1-1000 mg/kg/day, or any range therein, preferably from about 0.5-500 mg/kg/day, or any range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 1000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The methods of treatment described in the present invention may also be carried out using a pharmaceutical composition comprising any of the compounds as defined herein and a pharmaceutically acceptable carrier. The pharmaceutical composition may contain between about 0.1 mg and 1000 mg of the compound, or any range therein; preferably about 10 to 500 mg of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of anxiety and related disorders; bipolar depression and mania; depression; epilepsy and related disorders; epileptogenesis; glucose related disorders; lipid related disorders; migraine; obesity; pain; substance abuse or neuroprotection is required.

The daily dosage of the products may be varied over a wide range from 1.0 to 10,000 mg per adult human per day, or any range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500 and 1,000 milligrams of the active ingredient for the symptomatic adjustment of the dosage to the patient to be treated. An effective amount of the drug is ordinarily supplied at a dosage level of from about 0.1 mg/kg to about 1000 mg/kg of body weight per day, or any range therein. Preferably, the range is from about 0.5 to about 500 mg/kg of body weight per day, or any range therein. More preferably, from about 1.0 to about 250 mg/kg of body weight per day, or any range therein. More preferably, from about 0.1 to about 100 mg/kg of body weight per day, or any range therein. In an example, the range may be from about 0.1 to about 50.0 mg/kg of body weight per day, or any amount or range therein. In another example, the range may be from about 0.1 to about 15.0 mg/kg of body weight per day, or any range therein. In yet another example, the range may be from about 0.5 to about 7.5 mg/kg of body weight per day, or any amount of range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

Example 1

Preparation of the Compound of Formula (A)

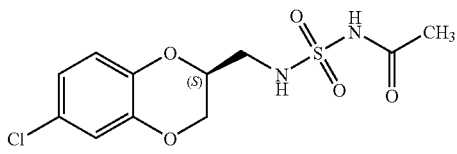

Acetyl chloride (0.71 g, 9.0 mmol) was added to (2S)-(−)-N-(6-chloro-2,3-dihydro-benzo[1,4]dioxin-2-ylmethyl)-sulfamide (2.1 g, 7.53 mmol) in 1,4-dioxane (30 mL) and the resulting mixture was brought to reflux under argon. After about 2 h, the resulting mixture was cooled to room temperature and evaporated in vacuo to yield a white solid (2.63 g). The white solid was purified using reverse phase HPLC (20-90% ACN) to yield the title compound as a white solid (1.03 g). The white solid was then recrystallized from ethyl acetate and hexane to yield the title compound as a white powdery solid.

mp: 184-185° C.

Optical rotation: $[\alpha]_D = -47.3°$ (c=1.20, $CH_3OH$)

Elemental Analysis:

Calculated: C, 41.19; H, 4.09; N, 8.73; Cl, 11.05; S, 10.00.

Measured: C, 41.15; H, 4.00; N, 8.62; Cl, 11.02; S, 9.87.

$H^1$ NMR (DMSO d6): δ 11.45 (s, 1H), 8.02 (dd, J=6.0, 6.0 Hz, 1H), 6.98 (dd, 1.4, 1.4 Hz, 1H), 6.89 (m, 2H), 4.28 (m, 2H), 4.0 (dd, J=6.4, 11.3 Hz, 1H), 3.19 (dd, J=6.0, 6.0 Hz, 2H), 1.94 (s, 3H).

Example 2

Oral Formulation—Prophetic Example

As a specific embodiment of an oral composition, 100 mg of the compound prepared as in Example 1 is formulated with sufficient finely divided lactose to provide a total amount of 580 to 590 mg to fill a size O hard gel capsule.

Example 3

In Vivo Assay: Maximal Electroshock Test (MES)

Anticonvulsant activity was determined using the MES test, run according to the procedure described in detail below. Swinyard E A, Woodhead J H, White H S, Franklin M R. Experimental selection, quantification, and evaluation of anticonvulsants. In Levy R H, et al., eds. *Antiepileptic Drugs*. 3rd ed. New York: Raven Press, 1989:85-102.

CF-1 male albino mice (25-35 g) were fasted for 16 hours before testing. Mice were randomly selected into control and test groups, with the animals dosed with vehicle or test compound, at varying concentrations, respectively. On the study date, at 30 minutes prior to shock, the mice were orally dosed with vehicle (0.5% methylcellulose) or test compound (200 mg/kg). Seizures were induced by trans-corneal electric shock using a 60-Hz alternating current, 50 mA, delivered for 0.2 sec. The mice in the test groups were subjected to electrical stimulus at time intervals between 15 minutes and 4 hours following administration of test compound. The shock resulted in an immediate full body tonic extension. The test was complete when the entire course of the convulsion has been observed (typically, less than 1 minute after electrical stimulation), and the mice were then immediately euthanized by carbon dioxide inhalation.

Abolition of the full body tonic extensor component of the seizure was taken as the endpoint of the test. Absence of this component indicated that the test compound had the ability to prevent the spread of seizure discharge through neural tissue. The $ED_{50}$ value of the test compound (calculated when appropriate) was the calculated dose required to block the hind limb tonic-extensor component of the MES-induced seizure in 50% of the rodents tested. A probit analysis was used to calculate the $ED_{50}$ and 95% fiducial limits (FL).

The compound of formula (A) was tested according to the procedure described above, with results as listed in Table 1 below. Results are listed as (number of mice with full body tonic extension prevented)/(total number of mice tested) (@ a given time).

TABLE 1

| | MES Activity | | | | |
| --- | --- | --- | --- | --- | --- |
| | 0.50 Hrs | 1.0 Hrs | 2 Hrs | 3 Hrs | 6 Hrs |
| Vehicle | 0/5 | | | | |
| Compound (A) 200 mg/kg po | 0/5 | 1/5 | 4/5 | 5/5 | 2/5 |
| Compound (S) 150 mg/kg po | | | | 5/5 | |

We claim:

1. A compound of formula (I)

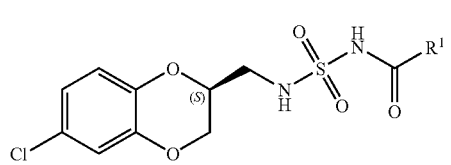

wherein

R¹ is selected from the group consisting of $C_{1-4}$alkyl;

or a pharmaceutically acceptable salt thereof;

provided that when R¹ is methyl, then the compound of formula (I) is present as an isolated or a substantially pure form.

2. A compound as in claim 1, wherein R¹ is selected from the group consisting of $C_{2-4}$alkyl.

3. A compound of formula (A)

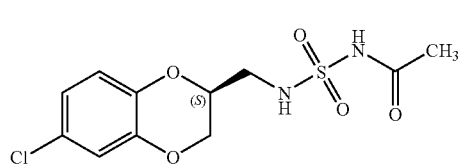

or a pharmaceutically acceptable salt thereof;

wherein the compound of formula (A) is present as an isolated or a substantially pure form.

4. A compound as in claim 3, wherein the compound of formula (A) is present as an isolated and a substantially pure form.

5. A compound as in claim 3, wherein the compound of formula (A) is present as an isolated, substantially pure form, having an (−) optical rotation.

6. A pharmaceutical composition comprising a pharmaceutically acceptable carrier and a compound of claim 1.

7. A pharmaceutical composition made by mixing a compound of claim 1 and a pharmaceutically acceptable carrier.

8. A process for making a pharmaceutical composition comprising mixing a compound of claim 1 and a pharmaceutically acceptable carrier.

9. A pharmaceutical composition comprising a pharmaceutically acceptable carrier and a compound of claim 3.

10. A pharmaceutical composition made by mixing a compound of claim 3 and a pharmaceutically acceptable carrier.

11. A process for making a pharmaceutical composition comprising mixing a compound of claim 3 and a pharmaceutically acceptable carrier.

12. A process for the preparation of a compound of formula (I)

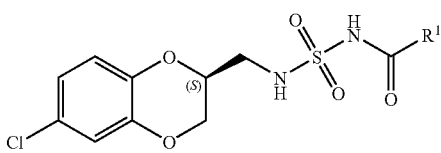

wherein

R¹ is selected from the group consisting of $C_{2-4}$alkyl or a pharmaceutically acceptable salt thereof; comprising

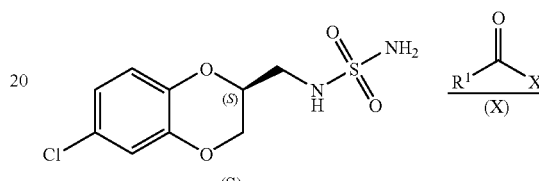

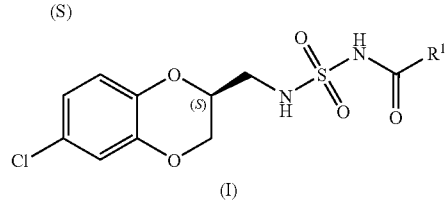

reacting a compound of formula (S) with a compound of formula (X), wherein X is a leaving group; in an organic solvent; to yield the corresponding compound of formula (I).

13. A process for the preparation of a compound of formula (A)

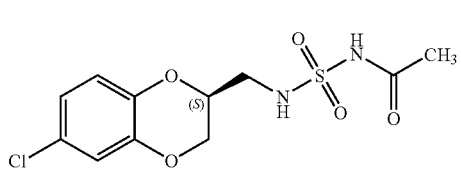

or a pharmaceutically acceptable salt thereof; comprising

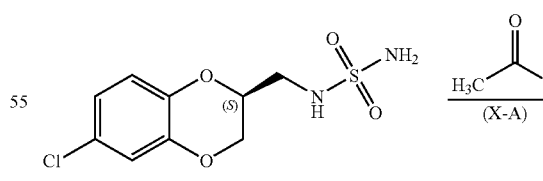

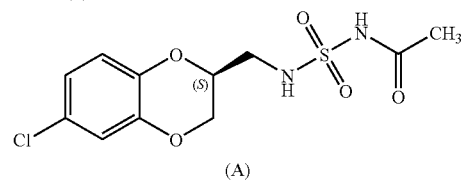

reacting a compound of formula (S) with a compound of formula (X-A), wherein X is a leaving group; in an organic solvent; to yield the corresponding compound of formula (A).

14. A process as in claim 13, wherein X is chloro; wherein the organic solvent is 1,4-dioxane; and wherein the compound of formula (S) is reacted with the compound of formula (X-A) at about solvent reflux temperature.

* * * * *